US012734059B2

(12) United States Patent
Peisner et al.

(10) Patent No.: US 12,734,059 B2
(45) Date of Patent: Sep. 15, 2026

(54) SELF-DONNING POWERED ORTHOTIC DEVICE

(71) Applicant: Myomo, Inc., Boston, MA (US)

(72) Inventors: Jeffrey Peisner, Durham, NC (US); Alida Pelli, Cambridge, MA (US); Samuel Kesner, Arlington, MA (US); Andrew Harlan, Somerville, MA (US); Christopher Long, Willoughby, OH (US)

(73) Assignee: Myomo, Inc., Burlington, MA (US)

( * ) Notice: Subject to any disclaimer, the term of this patent is extended or adjusted under 35 U.S.C. 154(b) by 486 days.

(21) Appl. No.: 18/334,783

(22) Filed: Jun. 14, 2023

(65) Prior Publication Data

US 2023/0320885 A1 Oct. 12, 2023

Related U.S. Application Data

(62) Division of application No. 16/219,016, filed on Dec. 13, 2018, now Pat. No. 11,712,360.

(60) Provisional application No. 62/598,388, filed on Dec. 13, 2017.

(51) Int. Cl.
*A61F 5/01* (2006.01)
*A61H 1/02* (2006.01)

(52) U.S. Cl.
CPC .......... *A61F 5/013* (2013.01); *A61H 1/0288* (2013.01); *A61F 2005/0155* (2013.01); *A61H 1/0274* (2013.01); *A61H 2201/0107* (2013.01); *A61H 2201/1207* (2013.01); *A61H 2201/1238* (2013.01); *A61H 2201/1642* (2013.01); *A61H 2201/165* (2013.01); *A61H 2201/169* (2013.01); *A61H 2201/5061* (2013.01); *A61H 2205/067* (2013.01)

(58) Field of Classification Search
CPC .... A61F 5/013; A61F 5/0118; A61F 5/05866; A61F 5/05875; A61F 5/10; A61F 2005/0155; A61F 2/586; A61H 1/0288; A61H 2205/067; A61H 2201/1238; A61H 2201/165
See application file for complete search history.

(56) References Cited

U.S. PATENT DOCUMENTS 4,790,301 A * 12/1988 Silfverskiold ........ A61F 5/0118 602/22
5,800,561 A 9/1998 Rodriguez
5,876,363 A 3/1999 Marx
6,565,563 B1 5/2003 Agee et al.
6,921,377 B2 7/2005 Bonutti
7,537,577 B2 5/2009 Phelan et al.
7,833,183 B2 11/2010 Padova
(Continued)

*Primary Examiner* — Keri J Nelson
(74) *Attorney, Agent, or Firm* — Merchant & Gould P.C.

(57) ABSTRACT

A powered orthotic device includes a brace, a finger engagement member, a thumb engagement member, and a hand actuator. The powered orthotic device includes an affixment member affixed to the brace, and a finger carrier assembly with a finger carrier to engage the fingers of the wearer, as well as a locking mechanism configured to be removably attached to the affixment member. The wearer dons the orthotic device, without assistance from another, by placing the set of fingers into the finger carrier and using a free hand of the wearer to affix the locking mechanism to the affixment member.

18 Claims, 23 Drawing Sheets

(56) References Cited

U.S. PATENT DOCUMENTS

| | | | | |
|---|---|---|---|---|
| 7,892,194 | B2 | 2/2011 | Farrell et al. | |
| 9,707,103 | B2 | 7/2017 | Thompson, Jr. et al. | |
| 9,764,190 | B2 | 9/2017 | Hoffman et al. | |
| 2014/0276268 | A1* | 9/2014 | Paffett | A61H 5/00 601/37 |
| 2016/0287422 | A1 | 10/2016 | Kelly et al. | |
| 2017/0333242 | A1 | 11/2017 | Hoffman et al. | |
| 2019/0167510 | A1* | 6/2019 | Dorr | A61H 9/0092 |

* cited by examiner 140
156
165
155
156
170
173
130
175
172
160
118
125
120
116
102
110
31'

SELF-DONNING POWERED ORTHOTIC DEVICE

RELATED APPLICATION

The present application is a divisional application of U.S. patent application Ser. No. 16/219,016, filed Dec. 13, 2018, which claims the benefit of U.S. Application No. 62/598,388, filed Dec. 13, 2017. The disclosures of these applications are incorporated by reference herein in their entireties.

TECHNICAL FIELD

The present invention relates to a powered orthotic device, and more particularly to, a powered orthotic device configured to enable its wearer to don the device without assistance from another person.

BACKGROUND ART

Stroke, brain injury, and other neuromuscular trauma survivors are often left with hemiparesis, or severe weakness, in certain parts of the body. The result can be impaired or lost function in one or more limbs. It has been shown that people can rehabilitate significantly from many of the impairments following such neurological traumas by, for example, following a rehabilitative exercise regime that includes the execution of familiar and functional tasks. Many of these people may use powered orthotic devices to assist and/or enhance their abilities to perform these tasks.

The configuration of conventional powered orthotic devices typically requires wearers to rely on other people for assistance in donning the devices. For example, an orthotic device may include a set of sheaths to house the fingers of the wearer's hand. Since neurological trauma may cause the wearer's fingers to remain in a curled position, the wearer's fingers must be uncurled to be inserted into the sheaths. Because uncurling the fingers would occupy the wearer's free hand, the wearer would require another person to fit the sheaths over the straightened fingers. Since the wearer cannot don the orthotic device unless another person is available to help him or her don the device, the wearer performs rehabilitative exercise regimes less frequently and consequently exhibits slower progress towards neurological recovery.

SUMMARY OF THE EMBODIMENTS

In accordance with one embodiment of the invention, an improved powered orthotic device, of the type that is removably attachable to an arm of a wearer, includes a brace and a finger engagement member that is coupled to the brace and that engages a set of fingers. The powered orthotic device includes a thumb engagement member and a hand actuator configured to cause motion of the finger engagement member relative to the thumb engagement member.

The powered orthotic device includes a locking mechanism affixed to the brace, and a finger carrier assembly. The finger carrier assembly includes a finger carrier that is shaped to engage the set of fingers of the wearer when the finger carrier assembly is attached to the locking mechanism. The finger carrier assembly also includes an affixment member configured to be removably attached to the locking mechanism. The locking mechanism and the finger carrier assembly together constitute the finger engagement member. Moreover, the wearer can don the orthotic device, without assistance by a second person, by attaching the orthotic device to the arm of the wearer, placing the set of fingers into the finger carrier, and using a free hand of the wearer to affix the affixment member to the locking mechanism.

The affixment member may include a loop and the locking mechanism may include a catch that removably retains the loop. The catch may be spring-loaded in a latched position. The locking mechanism may also include a release configured to disengage the loop from the catch, and the release may be configured to slide between a latched position that retains the loop and an unlatched position that disengages the loop. The affixment member may include a dual side release buckle and the locking mechanism may include a catch that removably retains the dual side release buckle. The affixment member may removably attach to the locking mechanism via magnetic force. In some embodiments, the affixment member is configured to attach to the locking mechanism via friction fit.

The finger carrier may include a set of receivers such that the wearer places a different finger in each receiver. Each receiver may be a groove, a ring, a sleeve, or a cup. The finger carrier assembly may include a rigid stem disposed between the finger carrier and the affixment member.

In some embodiments, the finger carrier assembly includes a set of cables coupling the finger carrier to the affixment member and a tightening mechanism coupled to the cables. The tightening mechanism is configured to adjust tension in the cables, thereby enabling the cables to become tight for the wearer to don the orthotic device, and to become slack for the wearer to doff the orthotic device.

In various embodiments, the finger carrier includes a permanently attached grip that is configured to provide an increased surface area for contacting an object, relative to the finger carrier. The grip may include a rigid plate, and an underside of the grip may include a textured surface to increase friction between the grip and an object to be grasped.

The locking mechanism may be disposed on a portion of the brace configured to be coupled to a dorsal surface of the wearer's hand or a lateral surface of the wearer's hand.

In some embodiments, the wearer places the set of fingers into the finger carrier before using a free hand of the wearer to affix the affixment member to the locking mechanism. In other embodiments, the wearer uses a free hand of the wearer to affix the affixment member to the locking mechanism before placing the set of fingers into the finger carrier.

In accordance with another embodiment of the invention, an improved powered orthotic device, of the type that is removably attachable to an arm of a wearer, includes a brace and a finger engagement member, coupled to the brace, to engage a set of fingers. The powered orthotic device includes a thumb engagement member and a hand actuator configured to cause motion of the finger engagement member relative to the thumb engagement member.

The powered orthotic device includes an affixment member affixed to the brace and a finger carrier assembly. The finger carrier assembly includes a finger carrier shaped to engage the set of fingers of the wearer when the finger carrier assembly is attached to the affixment member. The finger carrier assembly also includes a locking mechanism configured to be removably attached to the affixment member. The affixment member and the finger carrier assembly together constitute the finger engagement member. The wearer can don the orthotic device, without assistance by a second person, by attaching the orthotic device to the arm of the wearer, placing the set of fingers into the finger carrier, and using a free hand of the wearer to affix the affixment member on the brace to the locking mechanism on the finger carrier assembly. The powered orthotic device includes any of the features described above, in any combination.

In accordance with another embodiment of the invention, a method of donning a powered orthotic device by a wearer without assistance by a second person includes attaching the orthotic device to an arm of the wearer. The orthotic device includes a brace, a finger engagement member, a thumb engagement member, and a hand actuator. The finger engagement member is coupled to the brace and configured to engage a set of fingers. The finger engagement member includes a locking mechanism and a finger carrier assembly, and the finger carrier assembly includes an affixment member and a finger carrier shaped to engage the set of fingers. The hand actuator is configured to cause motion of the finger engagement member relative to the thumb engagement member.

The method may include placing the set of fingers of a hand of the wearer in the finger carrier of the finger carrier assembly. The method may include removably attaching, using a free hand of the wearer, the affixment member to the locking mechanism. The method may include placing each finger in the set of fingers in a distinct receiver of a set of receivers of the finger carrier. Each receiver may be a ring.

The method may include retaining a loop of the affixment member on a catch of the locking mechanism. The affixment member may removably attach to the locking mechanism via magnetic force. The locking mechanism may be disposed on a portion of the brace configured to be coupled to a dorsal surface of the wearer's hand or a lateral surface of the wearer's hand.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1:
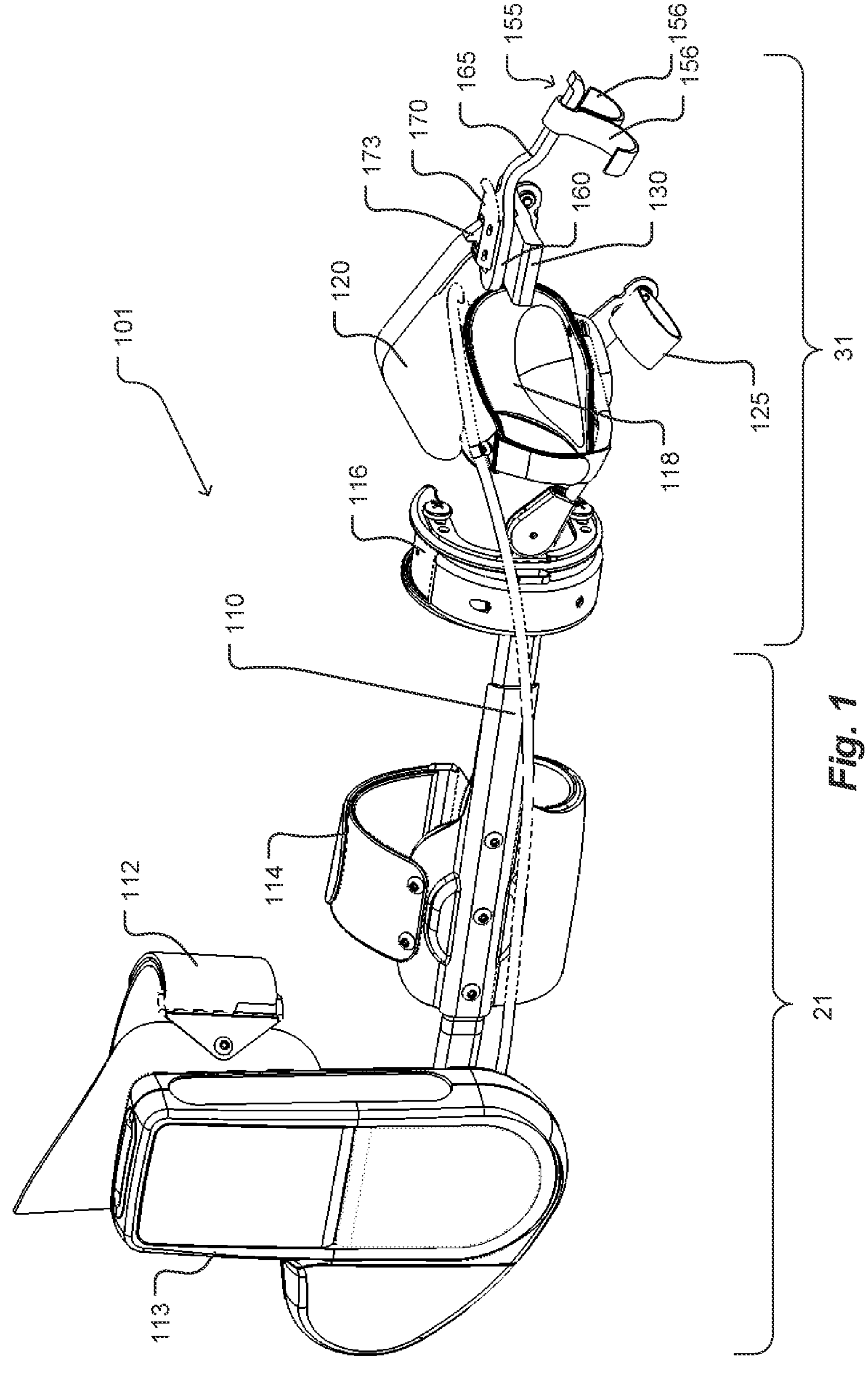
FIGS. 1 and 2 are perspective views, from the right side and the left side respectively, of an exemplary powered orthotic device 101, configured for use on the right arm, in accordance with an embodiment of the present invention.

Definitions. As used in this description and the accompanying claims, the following terms shall have the meanings indicated, unless the context otherwise requires:

A "set" includes at least one member.

An "orthotic device" is a device that supports weak or ineffective joints or muscles. An orthotic device is worn over existing body parts to support and/or restore function to a weakened or malformed body part.

A "finger engagement member", which may be operated by the wearer without assistance from another person, is a structure that maneuvers the fingers of a wearer's impaired hand into a straightened position and couples the straightened fingers to a hand actuator on a powered orthotic device.

A "finger carrier" is a structural component, of a finger engagement member, that engages at least one finger of the wearer's hand.

A "locking mechanism" is a structure configured to secure a "finger carrier" to the powered orthotic device.

An "affixment member" is a structure configured to be removably attached to the "locking mechanism" to secure the "finger carrier" at the particular position on the powered orthotic device.

A "finger carrier assembly" is a structure that includes a "finger carrier" and one of the "affixment member" or "locking mechanism".

Embodiments of the powered orthotic device include a finger engagement member that a wearer may apply to an impaired hand, using his or her other free hand. The configuration of the finger engagement member enables a wearer to don the powered orthotic device without assistance from another person. Since the wearer can don the powered orthotic device at will, the wearer can control the timing and frequency of his or her rehabilitative exercise regime, or perform tasks using the impaired hand when desired. As a result, the powered orthotic device grants the wearer a level of autonomy not provided by conventional orthotic devices.

Like conventional orthotic devices, the exemplary powered orthotic device is configured to enable the wearer to attach the orthotic device to a limb. For example, embodiments of the powered orthotic device may include straps, attached to a brace, which the wearer may wrap around parts of his or her body, such as an upper arm, a forearm, or both. The wearer may also insert his or her impaired hand into a hand support shell.

However, unlike the prior art, embodiments of the exemplary powered orthotic device include a finger engagement member that enables the wearer to uncurl the fingers of his or her impaired hand in tandem with engaging the fingers by the orthotic device. In some embodiments, the wearer engages the fingers of the impaired hand using a finger carrier assembly that may be removably attached to the powered orthotic device. When the finger carrier assembly is attached, the configuration of the finger engagement member maintains the fingers in a straightened position.

In further embodiments, the finger engagement member is irremovable from the orthotic device, and the wearer may manipulate the finger engagement member to engage the fingers of the impaired hand. For any of these embodiments, the wearer may operate the finger engagement member to release the fingers of the impaired hand, and subsequently doff the orthotic device.

Figure 2:
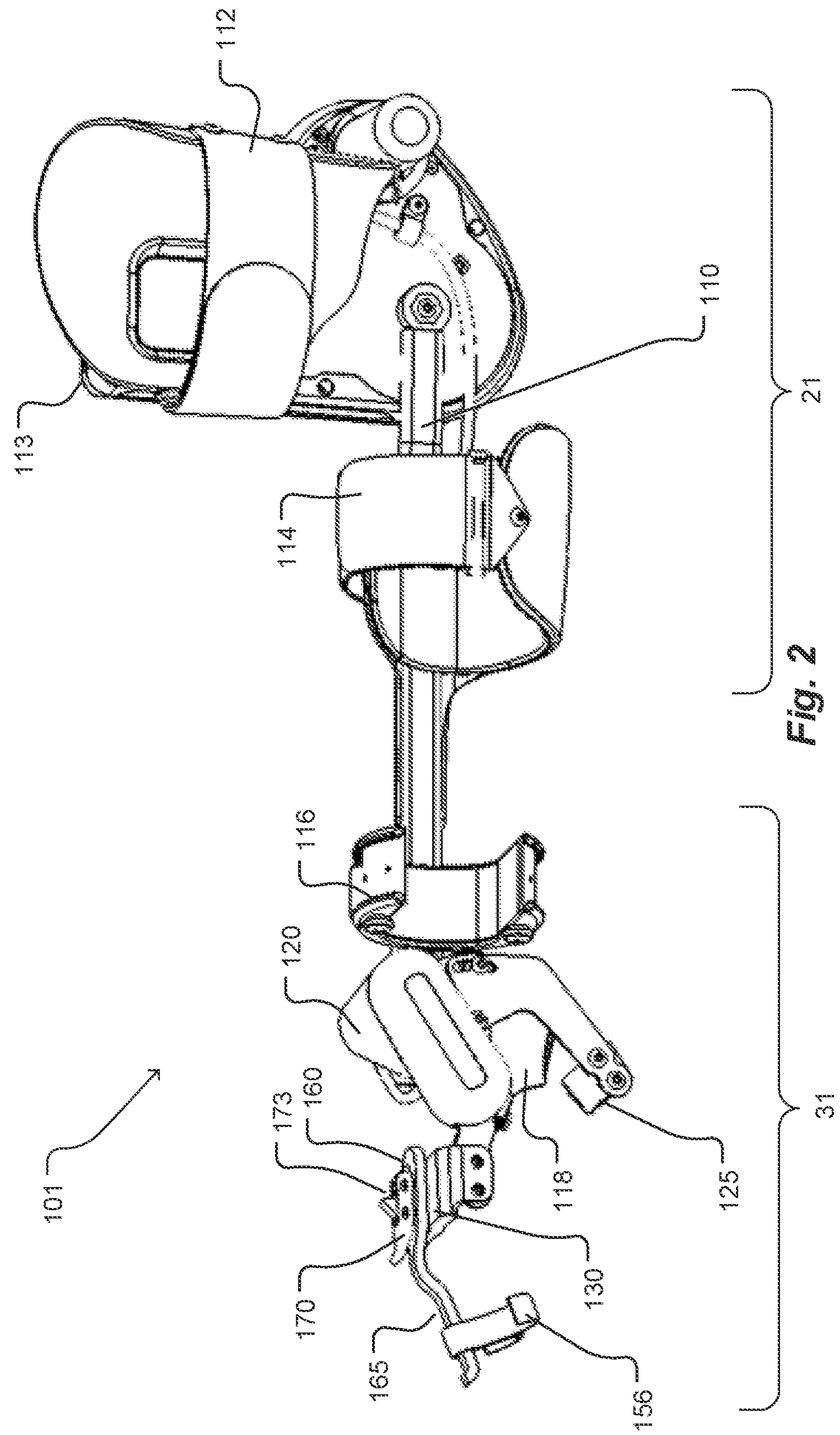

FIGS. 1 and 2 are perspective views, from the right side and the left side respectively, of an exemplary powered orthotic device 101 configured for use on the right arm, in accordance with an embodiment of the present invention. The powered orthotic device 101 includes a brace 110 that supports an arm assembly 21 and a hand assembly 31, which are structures for coupling the powered orthotic device 101 to an arm and a hand of the wearer, respectively. The arm actuator 113 of the arm assembly 21 is attached to one end of the brace 110 and includes a strap 112 configured to be wrapped and secured around an upper arm of the wearer. The arm assembly 21 includes another strap 114, attached to a midsection of the brace 110, configured to be wrapped and secured around a forearm of the wearer. Thus, the wearer may removably attach the powered orthotic device 101 to an arm by wrapping the straps 112, 114 around his or her upper arm and forearm, respectively. The arm actuator 113 is configured to cause motion of the brace 110 relative to the arm actuator 113, thereby causing motion of the forearm relative to the upper arm.

Figure 3:
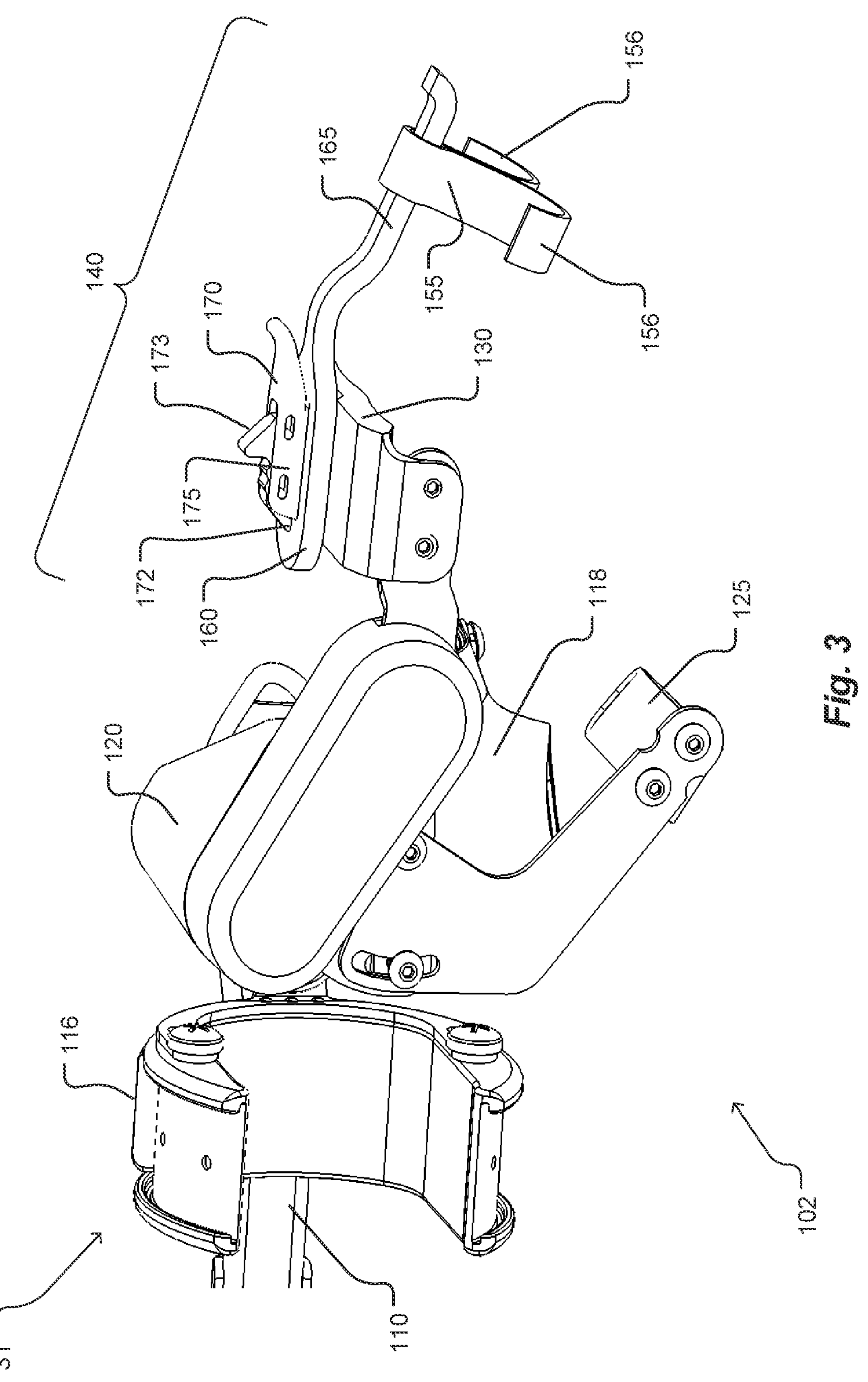
FIG. 3 is a left side perspective view of an orthotic device 102 similar to that of FIGS. 1 and 2, but configured for use on the left arm, showing detail of the structure for coupling to a hand of a wearer (e.g., the hand assembly 31'), in accordance with an embodiment of the present invention.

FIG. 3 is a left side perspective view of an orthotic device 102 similar to that of FIGS. 1 and 2, but configured for use on the left arm, showing detail of the structure for coupling to a hand of a wearer (e.g., the hand assembly 31'), in accordance with an embodiment of the present invention. The hand assembly 31' includes a cuff 116, such as a multi-articulated wrist cuff, and a hand support shell 118, both of which are attached to the brace 110. In some embodiments, to couple the hand assembly 31' to the wearer's hand, the wearer may first insert his or her wrist into the cuff 116 and guide the upper palm of the hand to rest upon the interior of the hand support shell 118. The wearer may also insert the thumb of the impaired hand into a thumb engagement member 125 coupled to the brace 110. Lastly, the wearer uses the finger engagement member 140 to couple the fingers of the impaired hand to the powered orthotic device 101, particularly, the hand actuator 120.

In the embodiments depicted in FIGS. 1-3, the finger engagement member 140 includes a finger carrier assembly 150 and a locking mechanism 170. The locking mechanism 170 is mounted on a finger support platform 130 on the orthotic device 101. The finger carrier assembly 150 includes a finger carrier 155, which, in this embodiment, includes a set of receivers 156. Each receiver 156 is configured to support a different finger of the wearer. The finger carrier 155 is coupled, via a stem 165, to an affixment member 160, and the affixment member 160 is configured to be removably attached to the locking mechanism 170, which, in turn, is affixed to the powered orthotic device 101 or 102.

A hand actuator 120 is attached to the brace 110, and coupled to both the thumb engagement member 125 and the finger support platform 130. When the wearer engages the fingers of the impaired hand with the finger carrier 155 and attaches the finger carrier assembly 150 to the locking mechanism 170, the hand actuator 120 causes the finger engagement member 140 to move relative to the thumb engagement member 125. Thus, when the wearer dons the powered orthotic device 101 or 102, the powered orthotic device 101 or 102 moves the wearer's fingers relative to his or her thumb so that the wearer regains some of the grasping functionality in his or her hand lost due to the neurological trauma.

Figure 4:
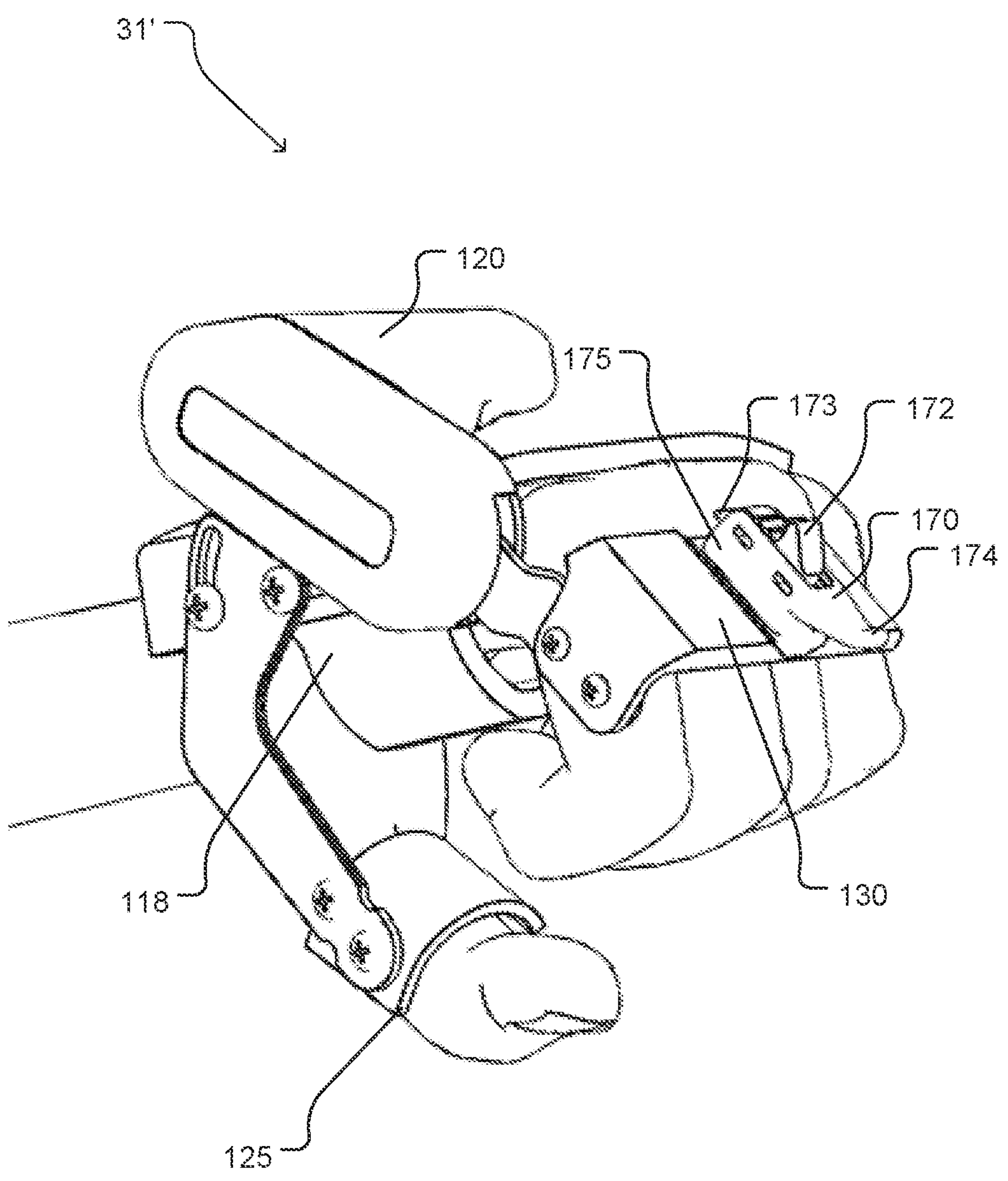
FIG. 4 is a three-quarter (showing the front and right side) perspective view of the hand assembly 31' of the powered orthotic device 102 of FIG. 3 as donned on the hand of the wearer, but without the finger carrier assembly 150.

FIG. 4 is a three-quarter (showing the front and right side) perspective view of the hand assembly 31' of the powered orthotic device 102 of FIG. 3 as donned on the hand of the wearer, but without the finger carrier assembly 150. In this figure, the wearer's thumb has been inserted in the thumb engagement member 125, and the upper palm rests upon the hand support shell 118. Due to neurological trauma, the fingers of the wearer may remain in a curled position.

Figure 5:
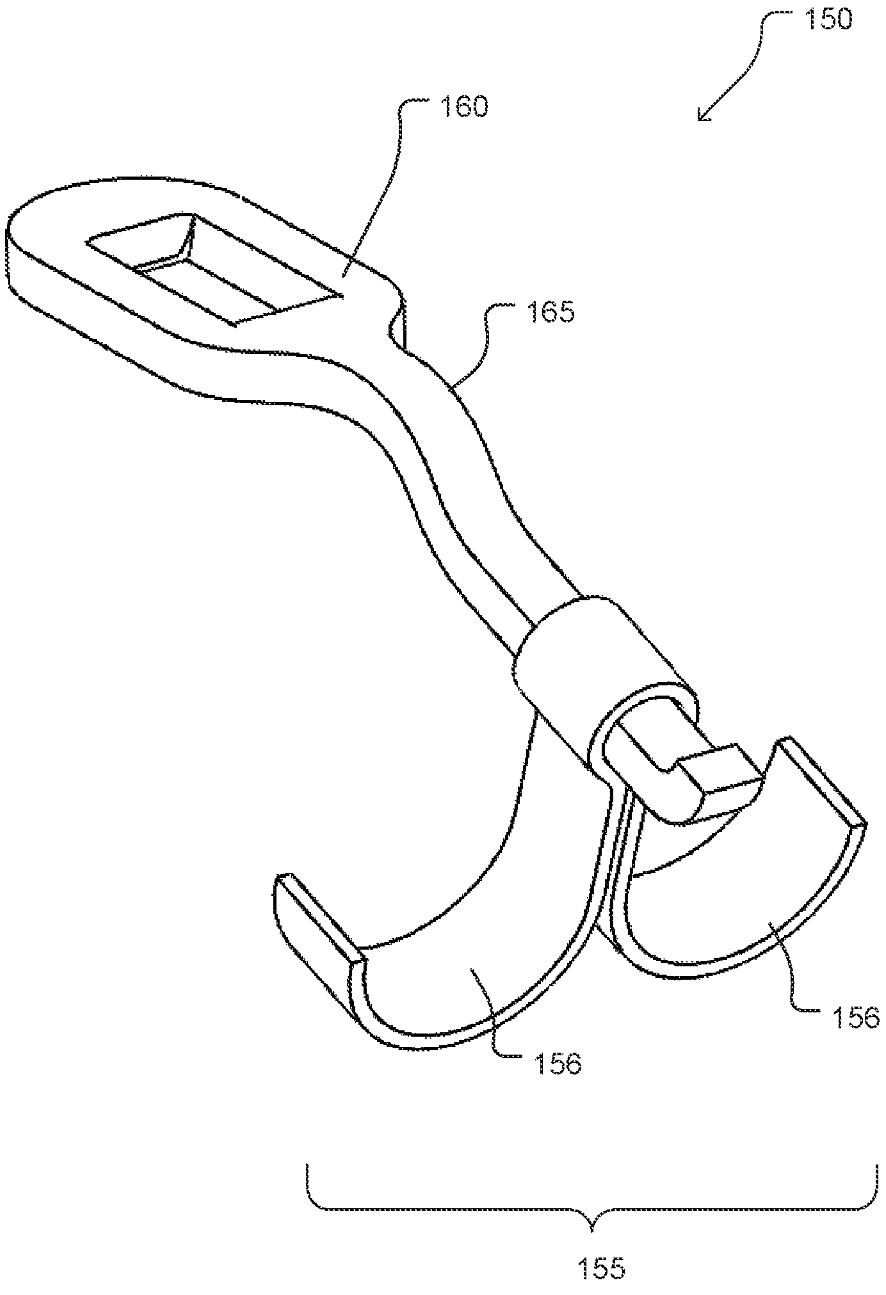
FIG. 5 is a three-quarter perspective view of a finger carrier assembly 150 for use with the hand assembly 31' of FIG. 4, in accordance with an embodiment of the present invention.

FIG. 5 is a three-quarter perspective view of a finger carrier assembly 150 for use with the hand assembly 31' of FIG. 4, in accordance with an embodiment of the present invention.

Figure 6:
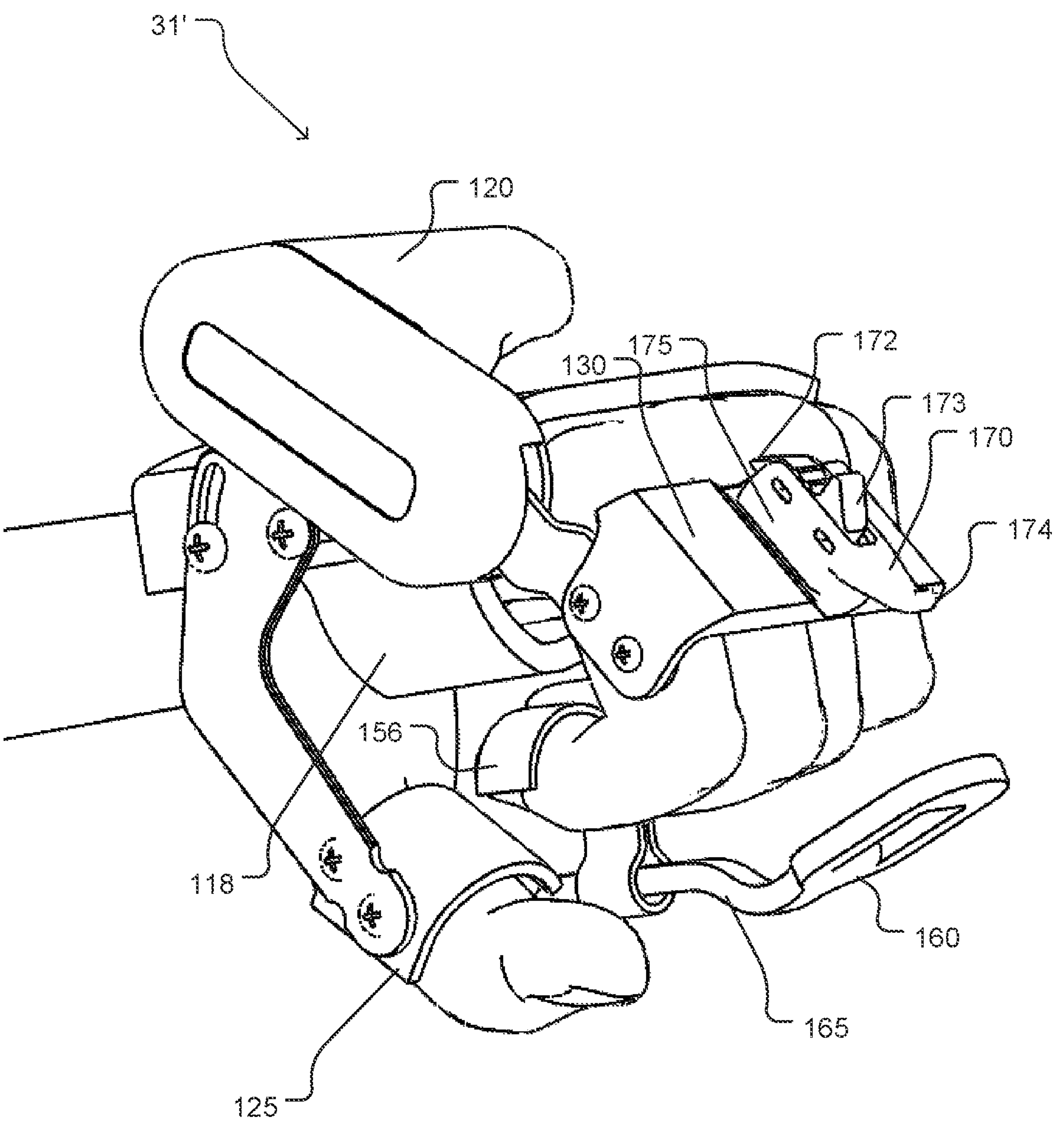
FIG. 6 is a three-quarter perspective view of the hand assembly 31' of the powered orthotic device 102 of FIG. 3 as donned on the hand of the wearer, with the finger carrier assembly 150 engaged by the fingers of the hand, in accordance with an embodiment of the present invention.

FIG. 6 is a three-quarter perspective view of the hand assembly 31' of the powered orthotic device 102 of FIG. 3 as donned on the hand of the wearer, with the finger carrier assembly 150 engaged by the fingers of the hand, in accordance with an embodiment of the present invention. To uncurl the fingers and couple the fingers to the powered orthotic device 101, the wearer may operate a finger carrier assembly 150 configured for use with the hand assembly 31'. Grasping the finger carrier assembly 150 by the affixment member 160 (in this embodiment, a loop 160) or the stem 165, the wearer may position each receiver 156 of the finger carrier 155 under a different finger of the impaired hand.

Figure 7:
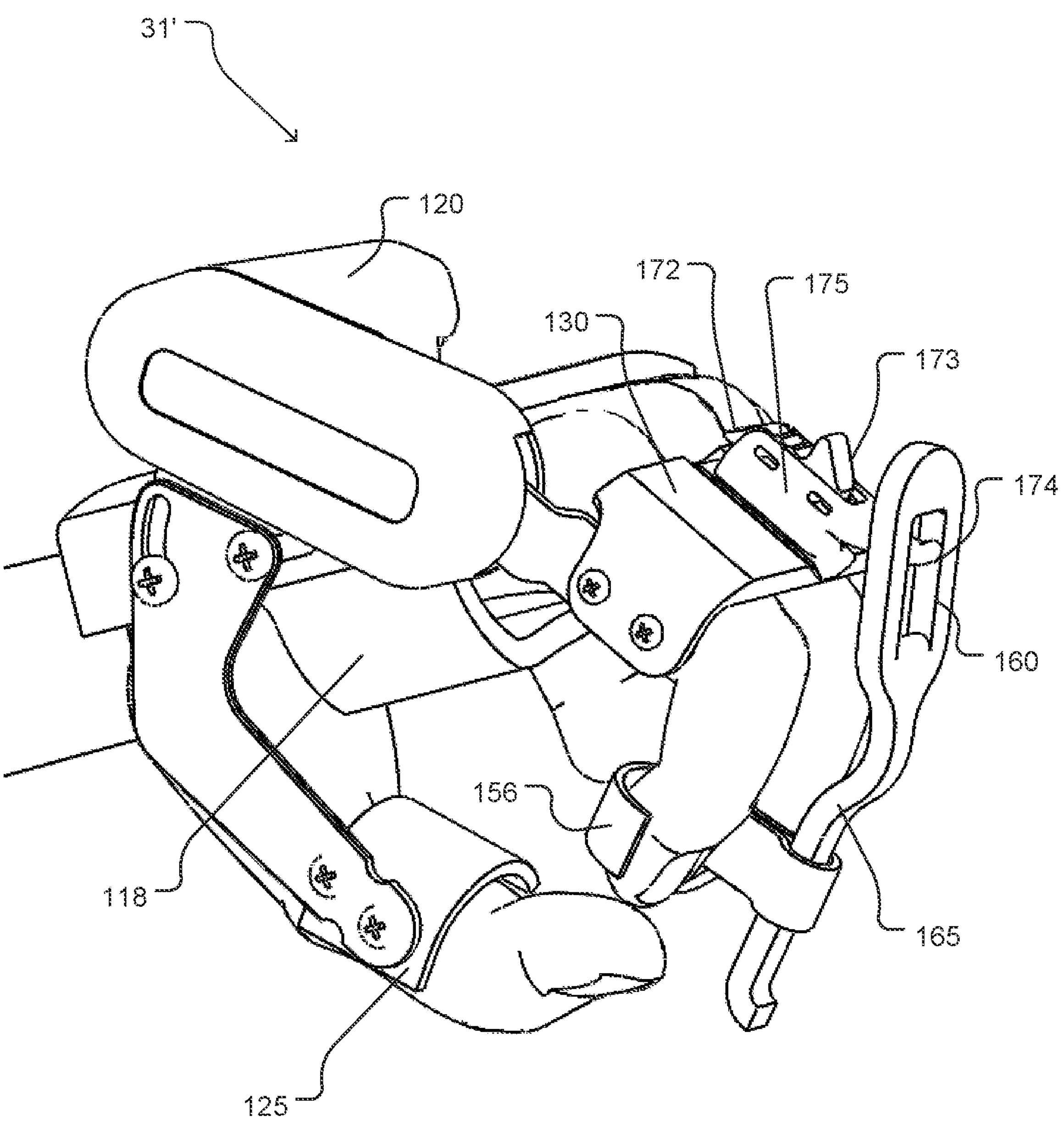
FIG. 7 is a three-quarter perspective view of the hand assembly 31' of FIG. 6, with the affixment member 160 of the finger carrier assembly 150 approaching the locking mechanism 170 that will maintain the fingers of the hand in a semi-straightened position, in accordance with an embodiment of the present invention.

FIG. 7 is a three-quarter perspective view of the hand assembly 31' of FIG. 6, with the affixment member 160 of the finger carrier assembly 150 approaching the locking mechanism 170 that will maintain the fingers of the hand in a semi-straightened position, in accordance with an embodiment of the present invention. As the wearer pulls the loop 160 or stem 165 towards the locking mechanism 170 on the finger support platform 130, the finger carrier assembly 150 straightens the curled fingers of the hand. Because drawing the fingers into a straightened position may tax the energy of the wearer, the wearer may wish to rest in the midst of his or her efforts. In the embodiments shown in FIGS. 1-4 and 6, the locking mechanism 170 includes a hook 174 configured to receive the loop 160 of the finger carrier assembly 150. When the loop 160 is suspended on the hook 174, the finger carrier assembly 150 maintains the fingers in a semi-straightened position. As a result, the hook 174 and finger carrier assembly 150 preserve some of the repositioning achieved by the wearer, and the wearer may rest before completing the attachment of the finger carrier assembly 150 to the locking mechanism 170.

Figure 8:
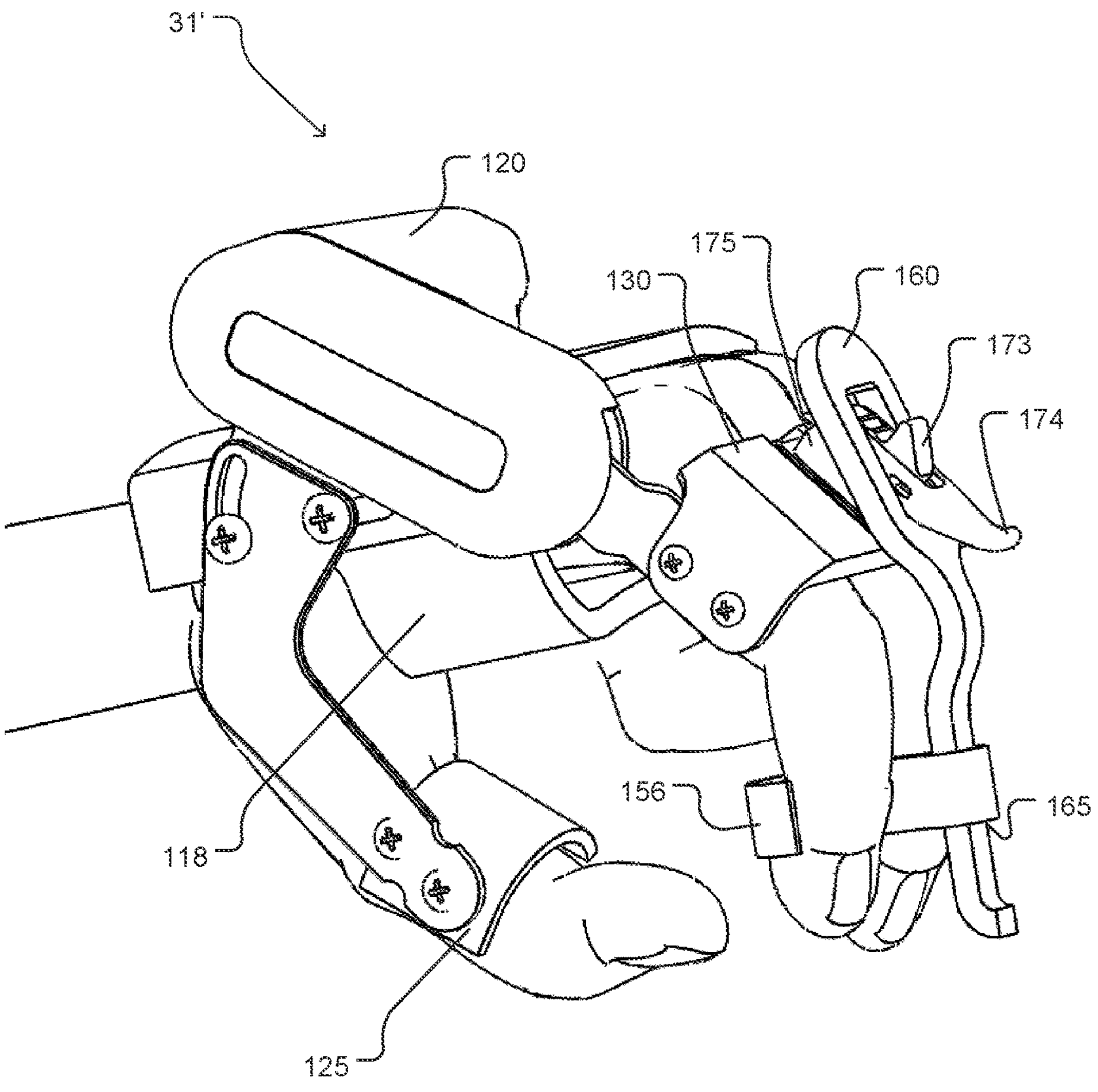
FIG. 8 is a three-quarter perspective view of the hand assembly 31' of FIG. 6, with the affixment member 160 of the finger carrier assembly 150 placed over the locking mechanism 170, immediately before being latched to it, in accordance with an embodiment of the present invention.
Figure 9:
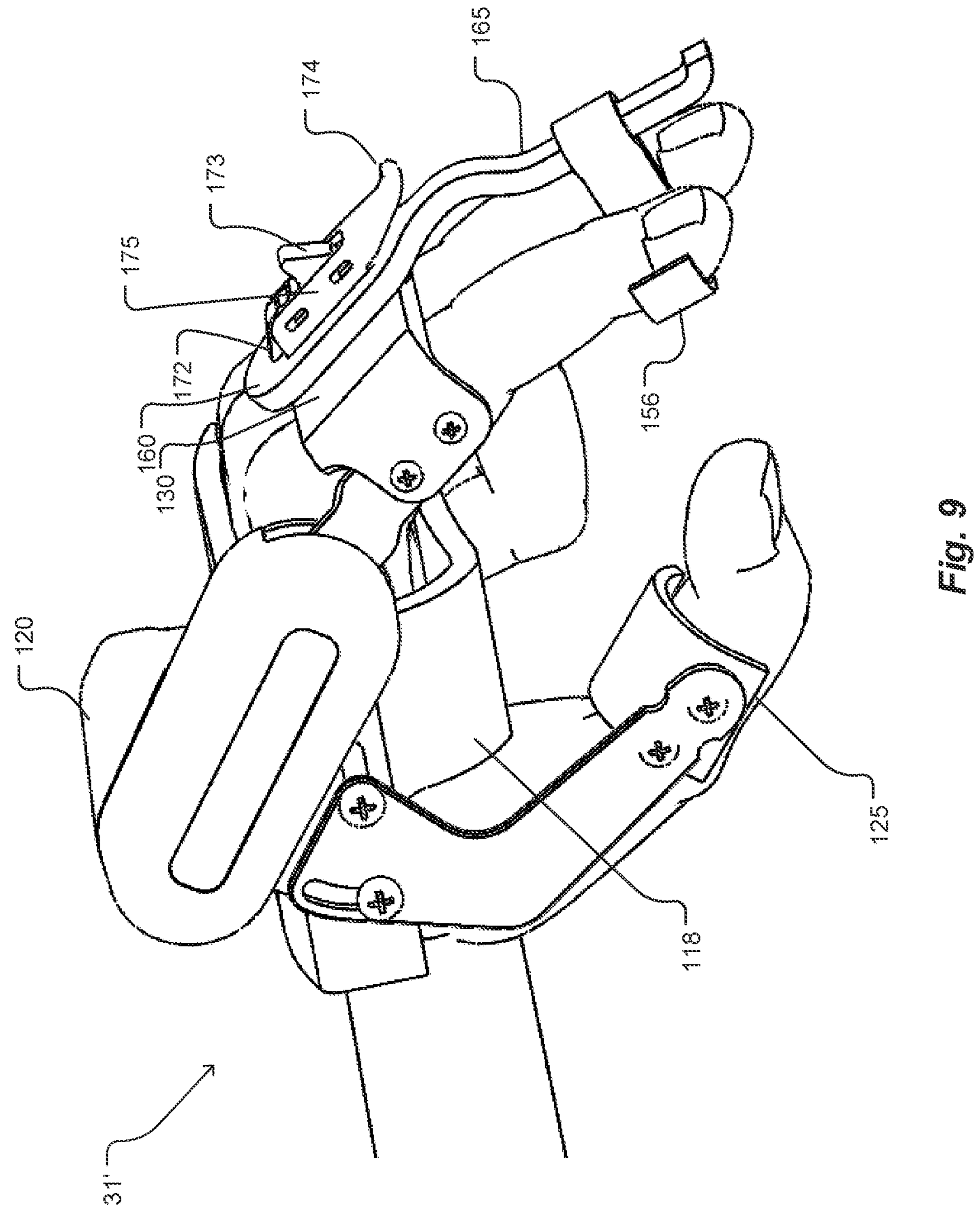
FIG. 9 is a three-quarter perspective view of the hand assembly 31' of FIG. 6, with the affixment member 160 of the finger carrier assembly 150 now latched to the locking mechanism 170, in accordance with an embodiment of the present invention.

FIG. 8 is a three-quarter perspective view of the hand assembly 31' of FIG. 6, with the affixment member 160 of the finger carrier assembly 150 placed over the locking mechanism 170, immediately before being latched to it, in accordance with an embodiment of the present invention, and FIG. 9 is a three-quarter perspective view of the hand assembly 31' of FIG. 6, with the affixment member 160 of the finger carrier assembly 150 now latched to the locking mechanism 170, in accordance with an embodiment of the present invention. To attach the affixment member 160 of the finger carrier assembly 150 to the locking mechanism 170, the wearer may pull the loop 160 over the base 175 of the locking mechanism 170. When the loop 160 is positioned around the base 175, the latch 172 secures the loop 160 and thus the attachment of the finger carrier assembly 150 to the locking mechanism 170.

Figure 10:
FIG. 10 is a side perspective view of the locking mechanism 170 of FIGS. 1-4 and 6-9, in accordance with an embodiment of the present invention.
Figure 10:
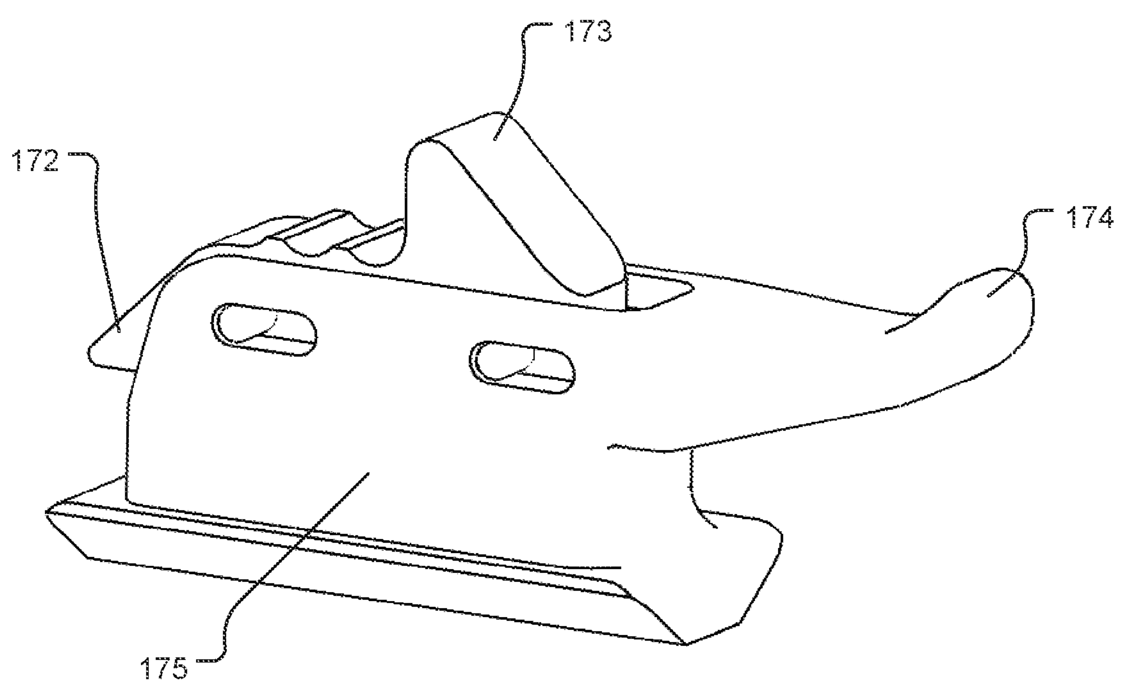

FIG. 10 is a side perspective view of the locking mechanism 170 of FIGS. 1-4 and 6-9, in accordance with an embodiment of the present invention. The locking mechanism 170 includes a latch 172 with a release 173, and in this embodiment, the latch 172 is a spring-loaded catch. The spring (not shown) is disposed inside of the base 175 and maintains the catch 172 in a protruded position from the base 175, i.e., a latched position.

Figure 11:
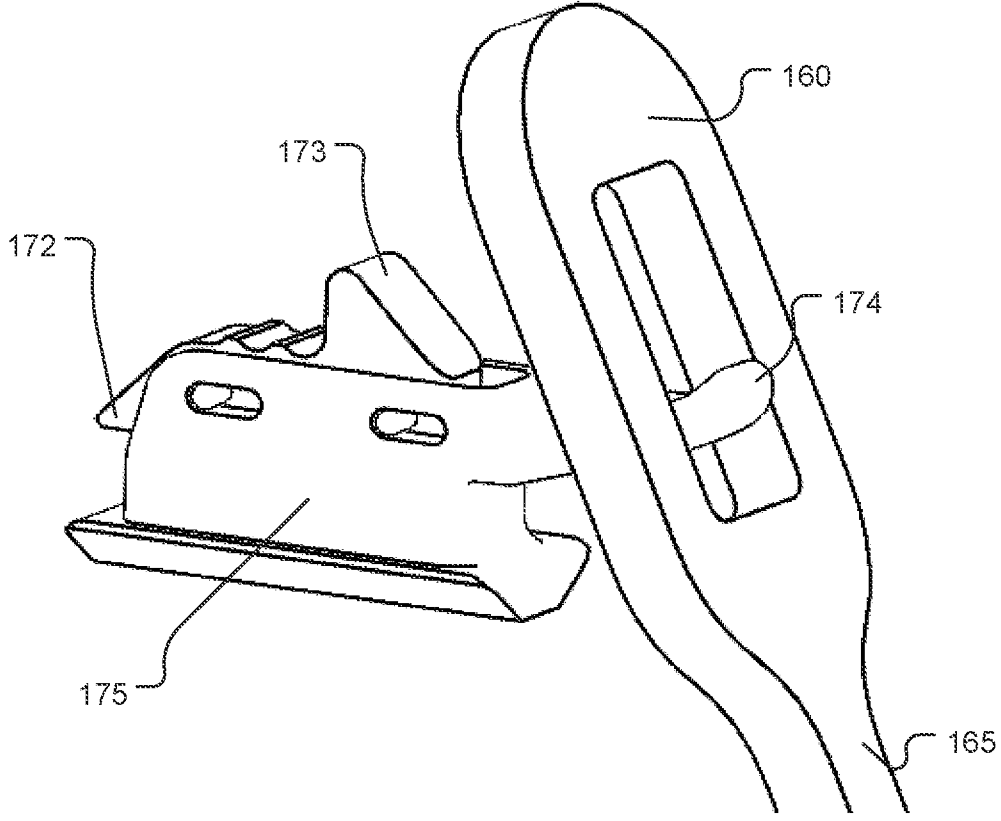
FIG. 11 is a side perspective view of the locking mechanism 170 of FIG. 10, shown in relation to the approaching affixment member 160, as in FIG. 7, in accordance with an embodiment of the present invention.
Figure 12:
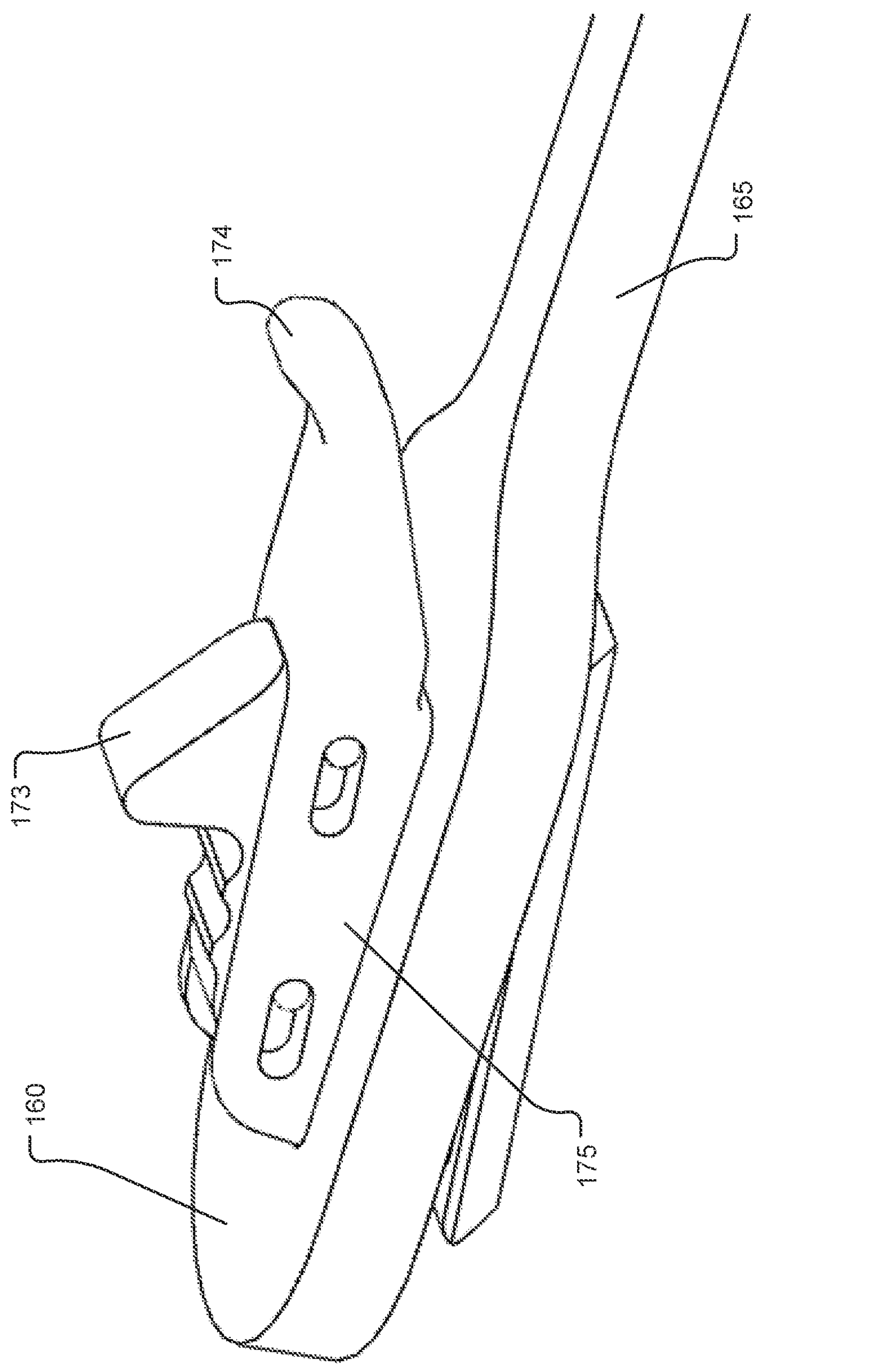
FIG. 12 is a side perspective view of the locking mechanism 170 of FIG. 10, shown with the affixment member 160 placed over the locking mechanism 170, immediately before being latched to it, as in FIG. 8, in accordance with an embodiment of the present invention.

FIG. 11 is a side perspective view of the locking mechanism 170 of FIG. 10, shown in relation to the approaching affixment member 160, as in FIG. 7, in accordance with an embodiment of the present invention, and FIG. 12 is a side perspective view of the locking mechanism 170 of FIG. 10, shown with the affixment member 160 placed over the locking mechanism 170, immediately before being latched to it, as in FIG. 8, in accordance with an embodiment of the present invention. To attach the affixment member 160 to the locking mechanism 170, the wearer pulls the loop 160 over the hook 174 and subsequently, the base 175. As the wearer positions the loop 160 around the base 175, the loop 160 pushes the catch 172 into the base 175, sliding the catch 172 into the unlatched position.

Figure 13:
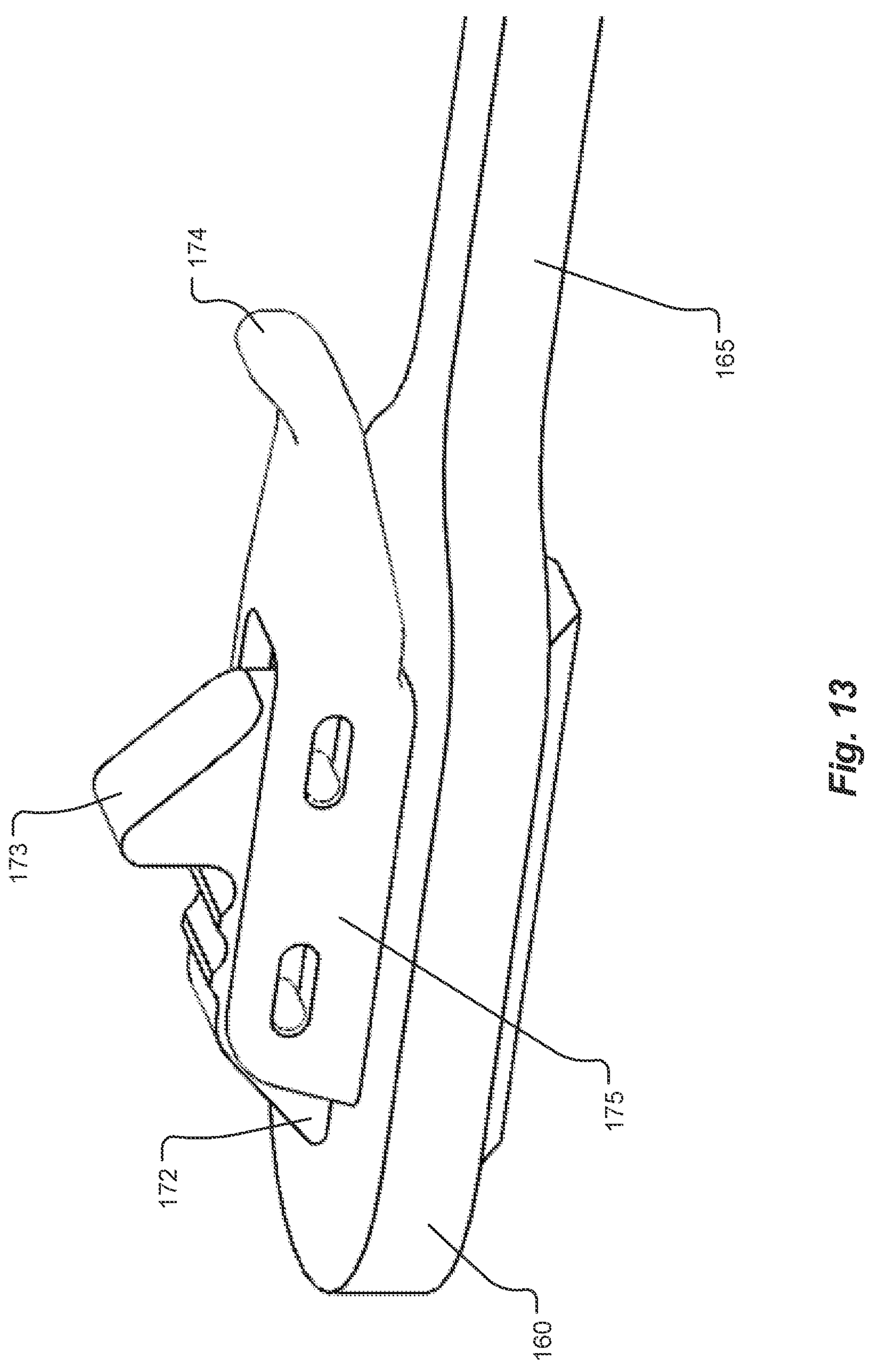
FIG. 13 is a side perspective view of the locking mechanism 170 of FIG. 10, shown with an affixment member 160 now latched to the locking mechanism 170, as in FIG. 9, in accordance with an embodiment of the present invention.

FIG. 13 is a side perspective view of the locking mechanism 170 of FIG. 10, shown with an affixment member 160 now latched to the locking mechanism 170, as in FIG. 9, in accordance with an embodiment of the present invention. After the wearer positions the loop 160 around the base 175 so as to lie flat on the finger support platform 130, the loop 160 no longer contacts the catch 172. The spring returns the catch 172 to the latched position and secures the finger carrier assembly 150 to the locking mechanism 170.

Due to the angle of the stem 165 relative to the loop 160, the finger carrier assembly 150 maintains the fingers of the impaired hand in a straightened position while the finger carrier assembly 150 remains attached to the locking mechanism 170. Because the hand actuator 120 is coupled to the finger support platform 130 and the thumb engagement member 125, the hand actuator 120 applies a force to cause motion of the finger engagement member 140 relative to the thumb engagement member 125. The hand actuator 120 may determine the force based on sensor signals received from one or more sensors (not shown) coupled to a part of the wearer's body (e.g., upper arm, forearm, wrist, hand, finger) or attached to the brace 110. Descriptions of the sensors that may be used by the orthotic device 101 may be found in U.S. application Ser. No. 15/183,279, entitled "Powered Orthotic Device and Method of Using Same" and filed Jun. 15, 2016, which is incorporated herein by reference in its entirety.

When the wearer is finished using the orthotic device 101, the wearer may operate the release 173 of the locking mechanism 170 to remove the finger carrier assembly 150. The wearer slides the release 173 to retract the catch 172 into the base 175 of the locking mechanism 170. Because the catch 172 no longer retains the loop 160, the wearer may lift the loop 160 over the base 175 to detach the finger carrier assembly 150. The wearer may further remove the impaired fingers from the finger carrier 155, and thereby allow his or her impaired hand to rest until the wearer next wishes to don the powered orthotic device 101.

Alternate Embodiments of the Powered Orthotic Device 101

In the embodiments depicted in FIGS. 1-4 and 6-9, the locking mechanism 170 is disposed on the powered orthotic devices 101 and 102, and the affixment member 160 is disposed on the finger carrier assembly 150. However, the positions of the locking mechanism 170 and affixment member 160 may be reversed, i.e., the locking mechanism 170 may be disposed on the finger carrier assembly 150, while the affixment member 160 is disposed on the orthotic device 101, 102. Thus, in these embodiments, the wearer removably attaches the affixment member 160 on the brace 110 to the locking mechanism 170 on the finger carrier assembly 150, to don the orthotic device 101, 102.

The powered orthotic devices 101 and 102 may use other types of affixment members 160 and/or locking mechanisms 170 that mechanically attach to one another. For example, the affixment member 160 may include at least one flexible tang. The wearer may depress the tang to insert the affixment member 160 into the locking mechanism 170, and when released, the tang may catch upon a ridge of the locking mechanism 170. Depressing the tang releases the tang from the ridge, and the wearer may remove the affixment member 160. One exemplary affixment member 160 with tangs is a dual side release buckle. In another example, the affixment member 160 is a buckle with a round tang, and the locking mechanism 170 includes a ring. The inner circumference of the ring matches the perimeter of the tang, and the wearer may depress the tang, insert the affixment member 160 into the locking mechanism 170, and release the tang to catch upon the ring. In other embodiments, the affixment member 160 removably attaches to the locking mechanism 170 via friction fit. For example, the affixment member 160 may include a plug that fits into a socket of a locking mechanism 170, although other types of male and female connectors may be used.

Alternative embodiments of the affixment members 160 and/or locking mechanisms 170 engage via magnetic force. Either the affixment member 160, the locking mechanism 170, or both may include ferromagnetic materials such as iron or nickel, or alloys thereof. To attach the finger carrier assembly 150 to the orthotic device 101 or 102, the wearer places the affixment member 160 sufficiently close to the locking mechanism 170 for one component of the finger engagement member 140 to attract the other. The wearer removes the finger carrier assembly 150 by pulling the affixment member 160 with enough force to overcome the magnetic attractive force between the affixment member 160 and locking mechanism 170.

Although the embodiments of FIGS. 1-3 and 5-9 depict the set of receivers 156 of the finger carrier 155 as a saddle, other types of receivers 156 may be used to engage the fingers of the impaired hand. The set of receivers 156 may include a set of grooves, a set of rings, a set of sleeves, or a set of cups (e.g., a set of thimbles). In these other embodiments, each groove, ring, sleeve, or cup, respectively, is configured to engage a different finger of the impaired hand. However, other embodiments of the finger carrier 155 may include a single receiver 156 to engage the impaired fingers collectively. For example, the receiver 156 may be a bar configured to be positioned under all four fingers of the impaired hand.

Figure 14:
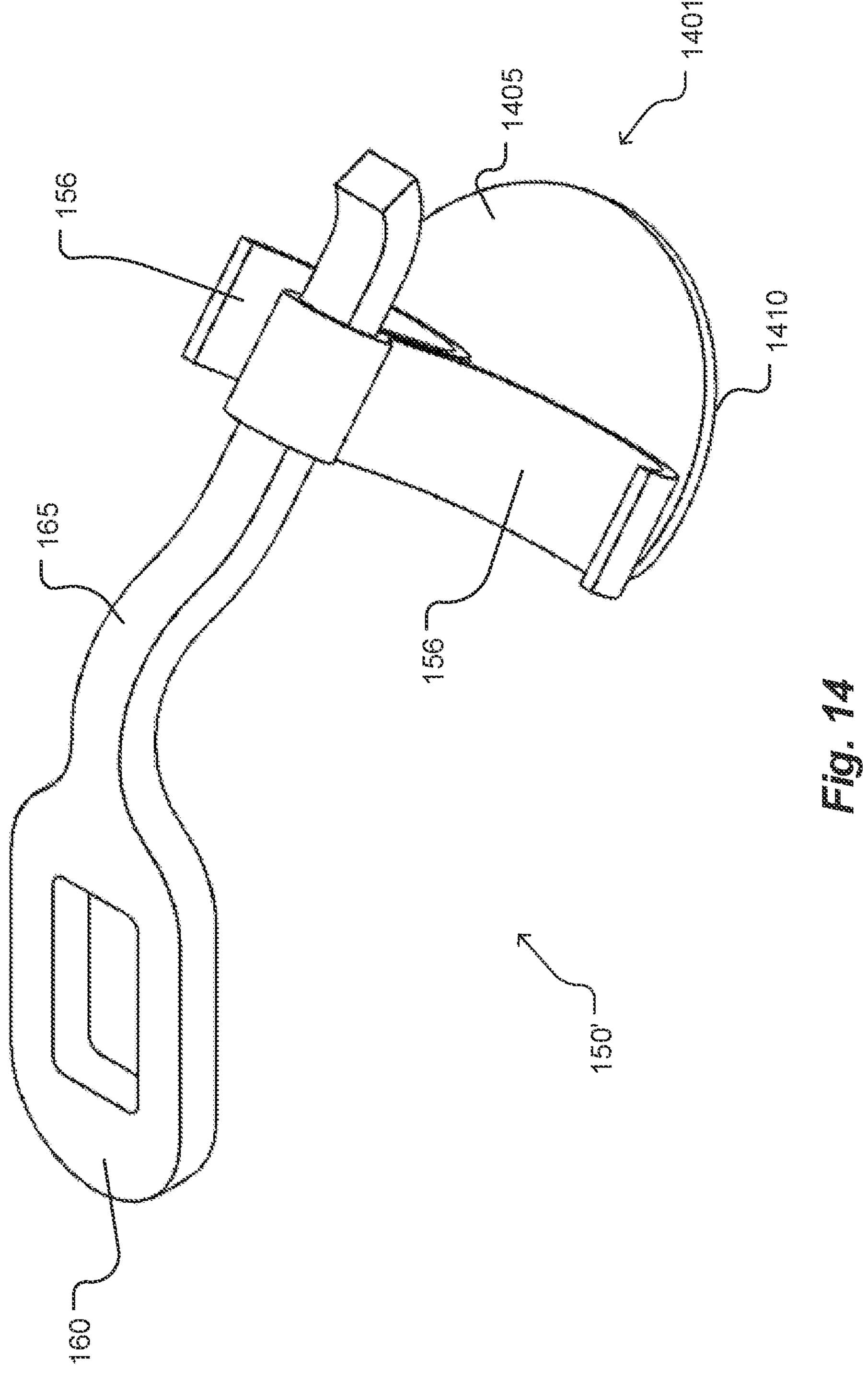
FIGS. 14-16 are three-quarter perspective views (showing the front and right side, the bottom and right side, and the front and left side, respectively) of a finger carrier assembly 150' with an integrated grip 1401, in accordance with an embodiment of the present invention.
Figure 15:
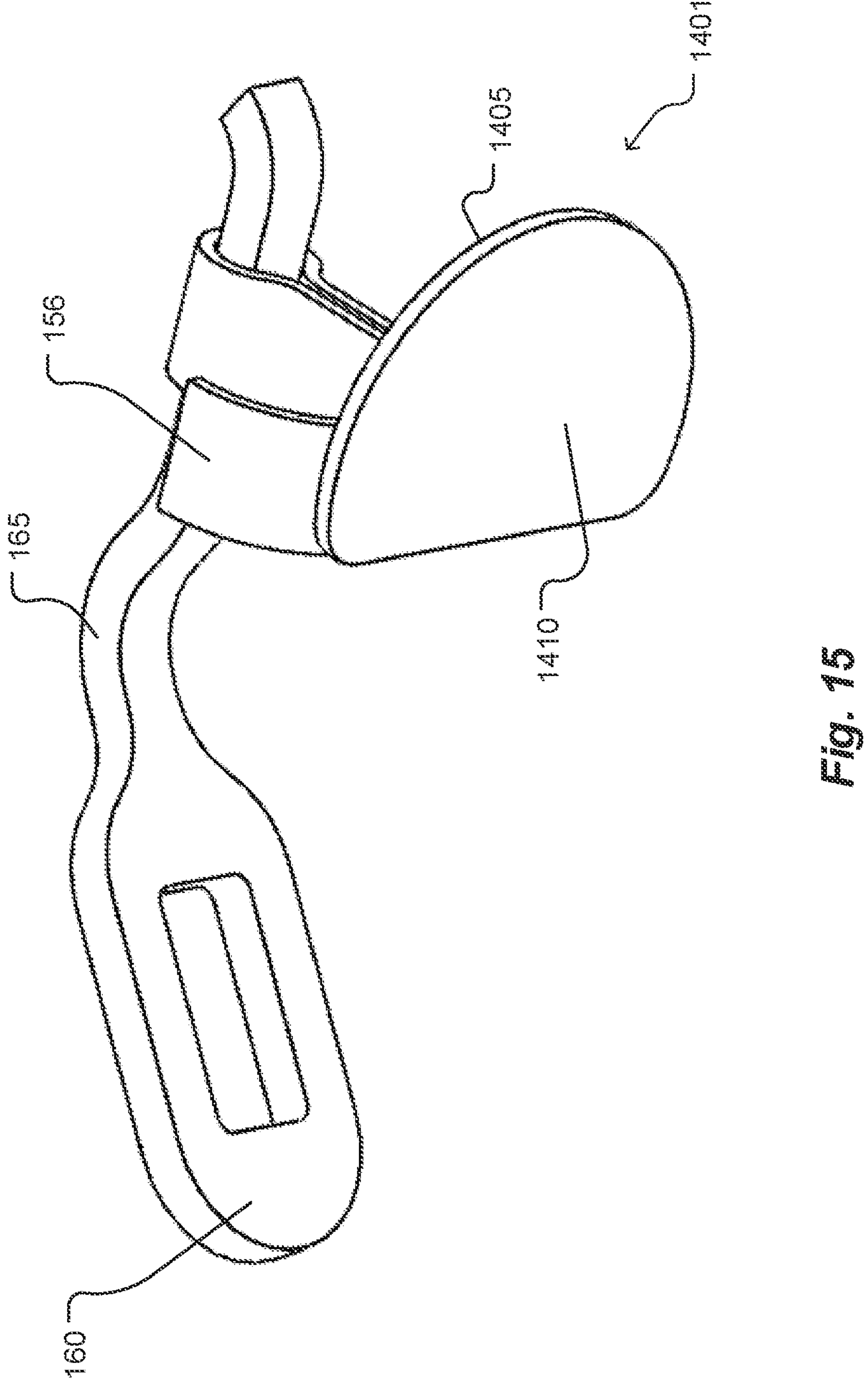
Figure 16:
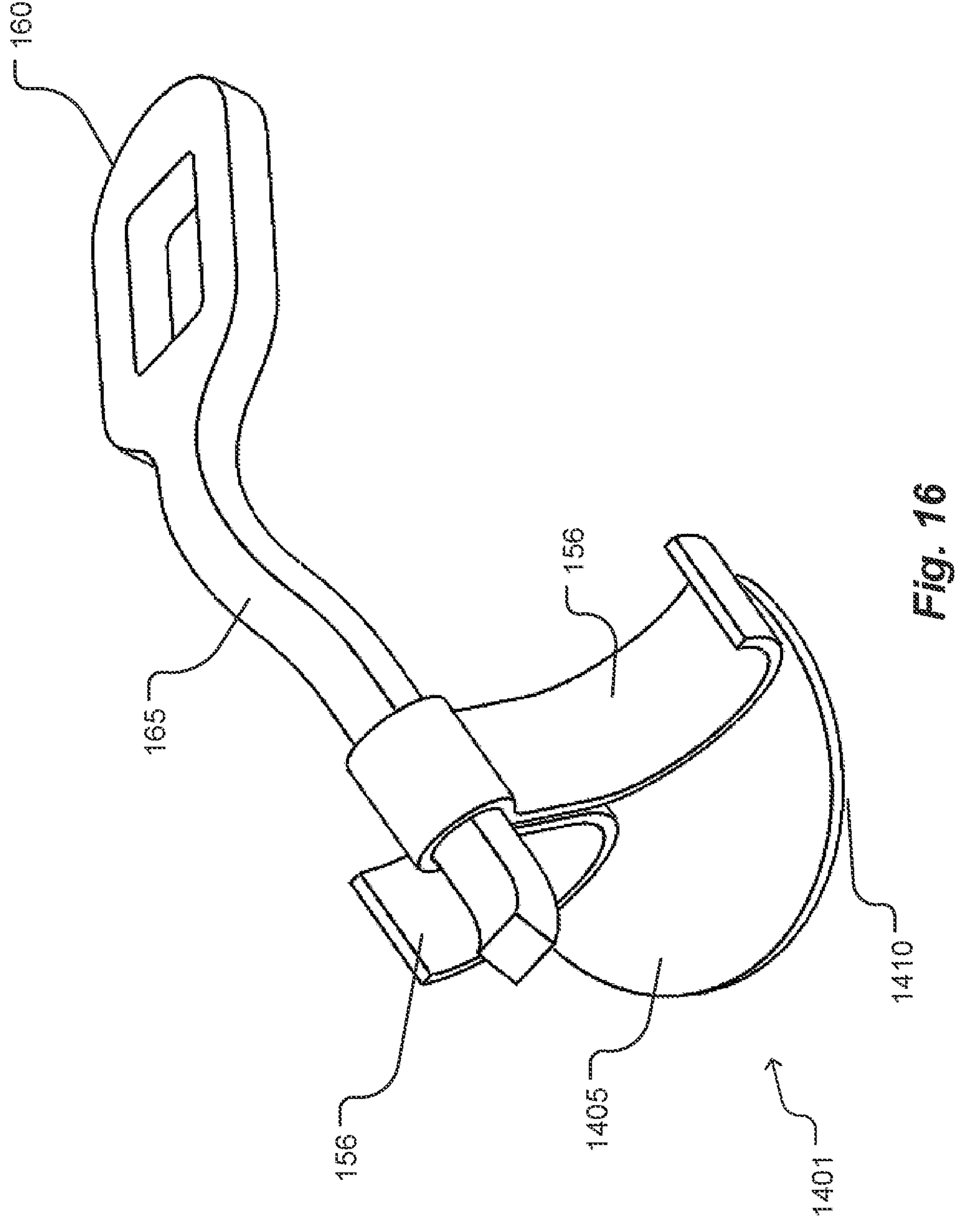
Figure 17:
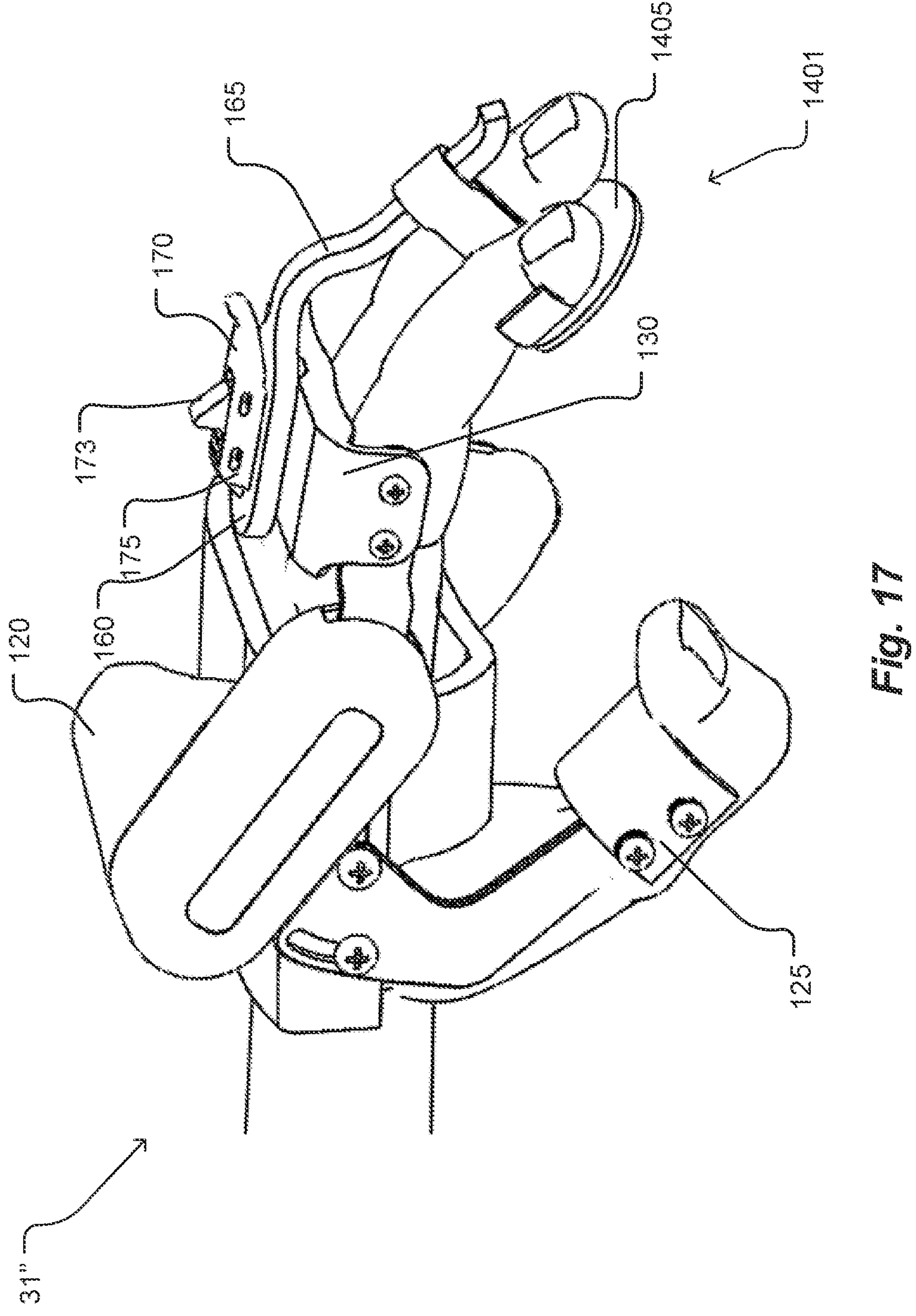
FIGS. 17-20 are three-quarter perspective views (showing the front and right side, the bottom and right side, the front and left side, and the bottom and left side, respectively) of the hand assembly 31" of the powered orthotic device 102 of FIG. 3, but with the finger carrier assembly 150' with the integrated grip 1401 of FIG. 14, as donned on the hand of the wearer.
Figure 18:
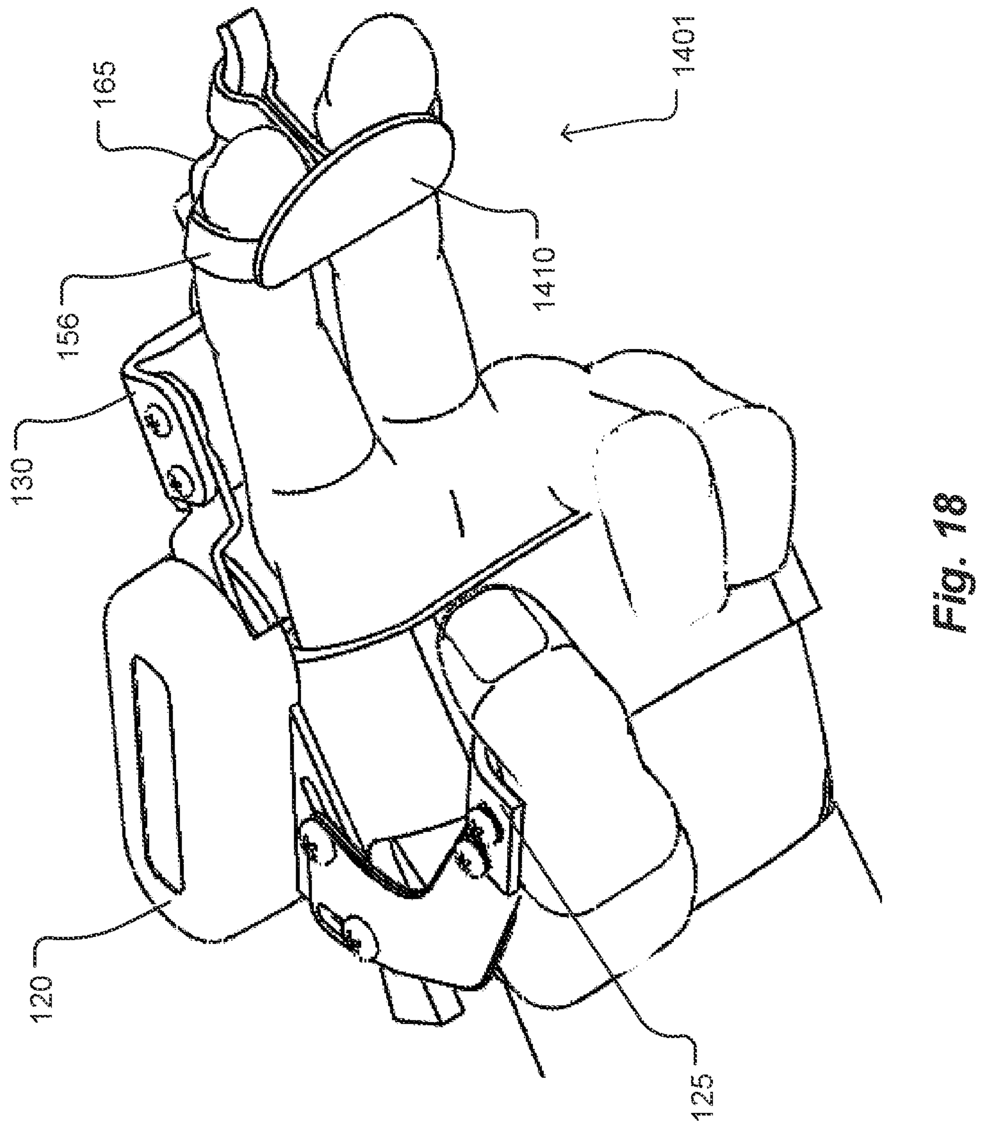
Figure 19:
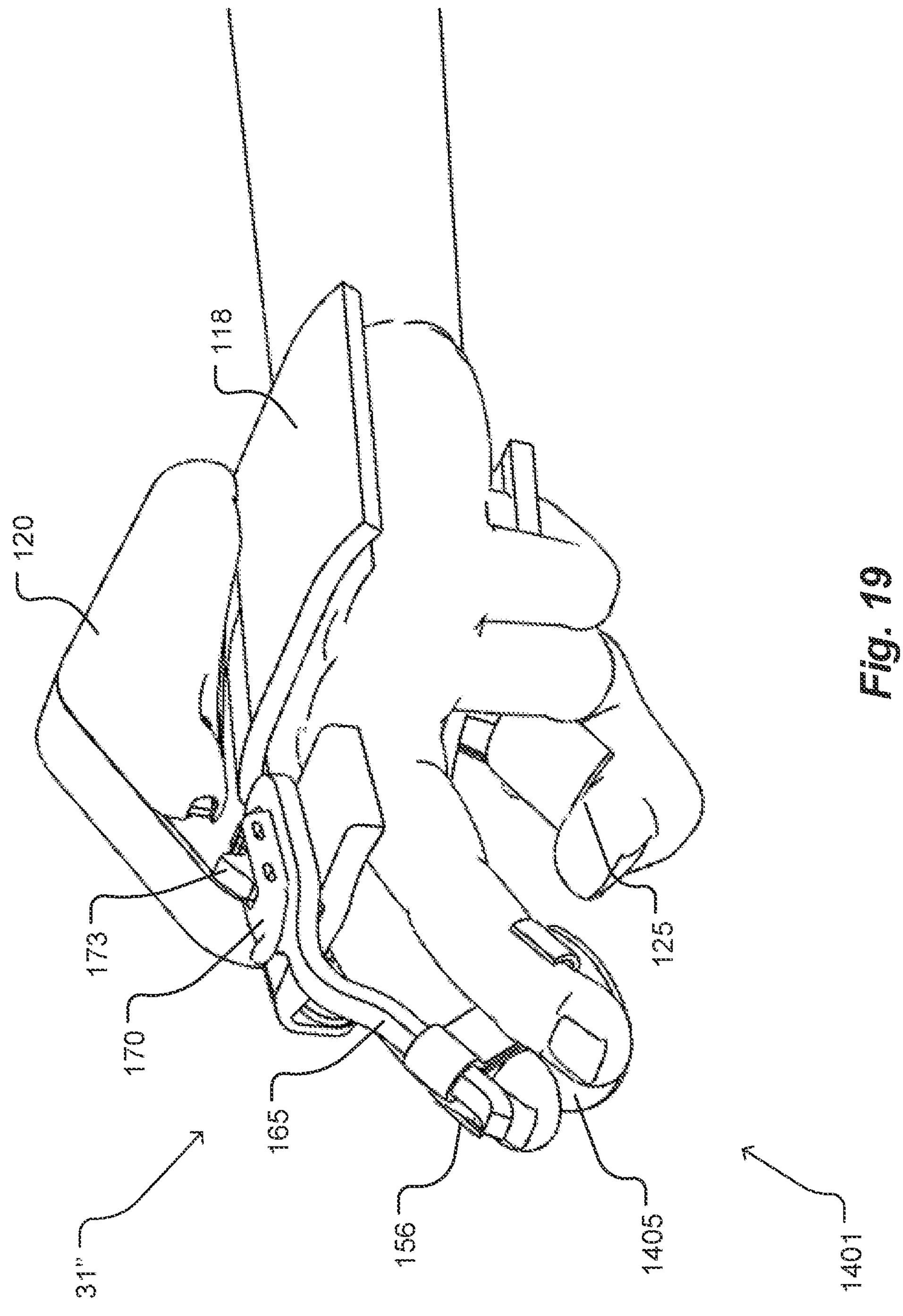
Figure 20:
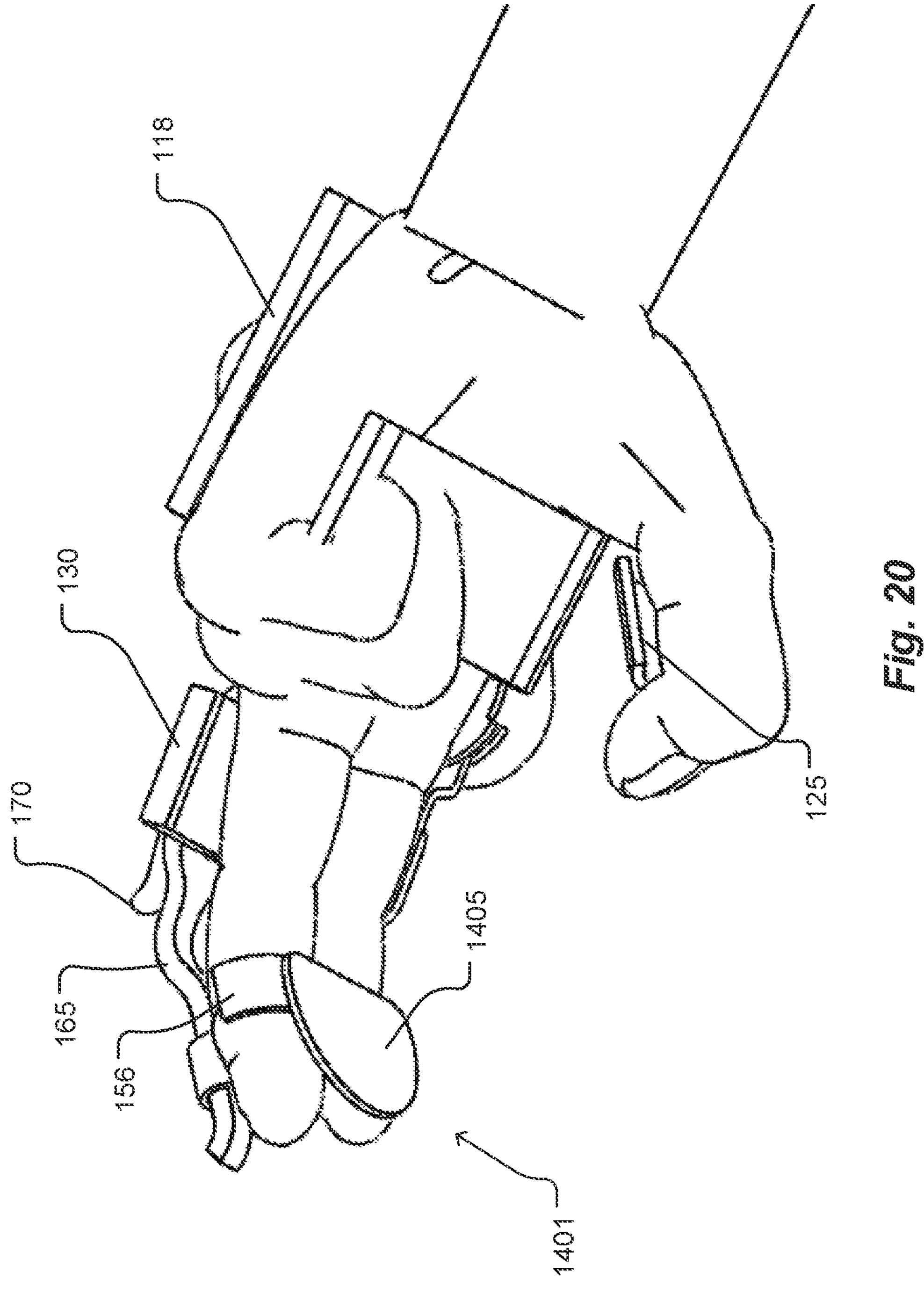

Moreover, additional embodiments of the finger carrier assembly 150' include a grip 1401 that improves the wearer's ability to grasp and/or control an object. FIGS. 14-16 are three-quarter perspective views (showing the front and right side, the bottom and right side, and the front and left side, respectively) of a finger carrier assembly 150' with an integrated grip 1401, in accordance with an embodiment of the present invention.

In this embodiment, the grip 1401 is a semi-circular plate 1405 affixed to the finger carrier 155. Compared to the receivers 156 of the finger carrier 155 alone, the flat surface 1410 on the underside of the plate 1405 provides an increased surface area for contacting an object. As a result, the grip 1401 enables the wearer to exert a larger amount of friction against the object, and consequently, superior control over the object. In this manner, the grip 1401 improves the security of any object within the wearer's grasp. Thus, when the wearer uses a finger carrier assembly 150' with the grip 1401, objects are less likely to slip from the wearer's hand as the wearer moves around or manipulates the objects.

FIGS. 17-20 are three-quarter perspective views (showing the front and right side, the bottom and right side, the front and left side, and the bottom and left side, respectively) of the hand assembly 31" of the powered orthotic device 102 of FIG. 3, but with the finger carrier assembly 150' with the integrated grip 1401 of FIG. 14, as donned on the hand of the wearer. As shown in these figures, the underside of the grip 1401 may match, or even extend beyond, the reach of the wearer's fingers, to improve the wearer's grasp of any object.

Although the embodiment of the grip 1401 depicted in FIGS. 14-20 is a semi-circulate plate 1405, other embodiments may assume alternative form factors. For example, the grip 1401 may be a plate that is circular, oval, or rectangular. In many embodiments, the plate 1405 may be rigid, whereas in other embodiments, the plate 1405 may be supple. The rigidity of any given plate 1405 may be tailored to the nature of the object to be grasped.

In various embodiments, the grip 1401 may have a curved surface, in lieu of the flat surface 1410, and the wearer may match the curvature of the grip 1401 with the curvature of an object to be grasped. For example, suppose the wearer wishes to grasp a can. The wearer can select a finger carrier assembly 150' whose integrated grip 1401 has a curved surface comparable to that of the can. After donning the powered orthotic device 102, the wearer may position the grip 1401 against the can before tightening his or her grasp. Because the curved surface of the grip 1401 is configured for the object, the wearer can grasp the object more securely, compared to the receivers 156 depicted in FIG. 5.

Additionally, the flat surface 1410 may be textured to increase friction between the grip 1401 and an object. In some embodiments, the flat surface 1410 may include a grid of raised bumps. Alternatively, the flat surface 1410 may include a set of grooves. In another embodiment, the underside of the grip 1401 includes ridges arranged in a cross-hatched pattern.

Furthermore, although the grip 1401 in the embodiment of FIGS. 14-20 is integrated with the finger carrier assembly 150', in other embodiments, the grip 1401 may be removably attachable to the receivers 156. For example, the grip 1401 may include two clips, each configured to be removably attached to a separate receiver 156 of the finger carrier 155. In another example, the grip 1401 may removably attach to the receivers 156 via magnetic force, via the ferromagnetic materials described above in relation to embodiments of the affixment members 160 and locking mechanisms 170. The grip 1401 may include elastic loops, such that the wearer threads an end of each receiver 156 through a separate loop to secure the grip 1401 to the finger carrier 155. Thus, for embodiments in which the grip 1401 is removably attachable to the finger carrier assembly 150', the wearer may select a particular grip 1401 that would be most effective in grasping a desired object.

Furthermore, in lieu of a rigid stem 165, the finger carrier assembly 150 may include a set of cables (not shown) coupling the finger carrier 155 to the affixment member 160. The set of cables may be coupled to a tightening mechanism (not shown), and the wearer may operate the tightening mechanism to adjust the tension in the individual cables. In this embodiment, to don the powered orthotic device 101, the wearer operates the tightening mechanism to loosen the cables. While the cables are slack, the wearer engages the fingers of the impaired hand with the finger carrier 155 and affixes the affixment member 160 to the locking mechanism 170. The fingers remain curled due to the lack of tension in the cables. However, as the wearer tightens the cables, the tension pulls the fingers into a straightened position. In further embodiments, the set of cables and their associated tightening mechanism may be replaced with other flexible materials capable of maintaining the fingers in a straightened position, such as a set of elastic materials.

In various embodiments of the powered orthotic device 101, the finger carrier assembly 150 may attach to the powered orthotic device 101 in different locations. The embodiments of FIGS. 1-4 and 6-9 depict the locking mechanism 170 disposed on a portion of the brace 110 configured to be coupled to the dorsal surface of the wearer's impaired hand. However, the locking mechanism 170 may be disposed on a portion of the brace 110 configured to be coupled to a lateral surface of the wearer's hand, at the wrist cuff 116, or any other location on the powered orthotic device 101. In any of these embodiments, the stem 165 of the finger carrier assembly 150 is reconfigured to permit engagement of the wearer's fingers as demonstrated in FIGS. 1-13, regardless of the location of the locking mechanism 170.

In alternate embodiments, the finger carrier assembly 150 is permanently affixed to the finger support platform 130, instead of being removably attachable. The finger carrier assembly 150 is configured to be operated by the wearer to engage or disengage from the fingers of the impaired hand. For example, the finger carrier assembly 150 may include a bar linkage configured to slide between different positions. By extending the bar linkage, the wearer positions the bar linkage to support and/or straighten the fingers of the impaired hand. By retracting the bar linkage (e.g., towards the wearer's wrist), the bar linkage releases the fingers. The powered orthotic device 101, 102 may include a locking mechanism that, when engaged, prevents the bar linkage from sliding from its current position. Alternatively, the bar linkage is coupled to a hinge, and adjusting the hinge changes the position of the bar linkage relative to the fingers of the wearer's impaired hand. Other structures for supporting the fingers, such as a truss, as well as other mechanisms for changing the position of the permanently attached finger carrier assembly 150, may be used.

Figure 21:
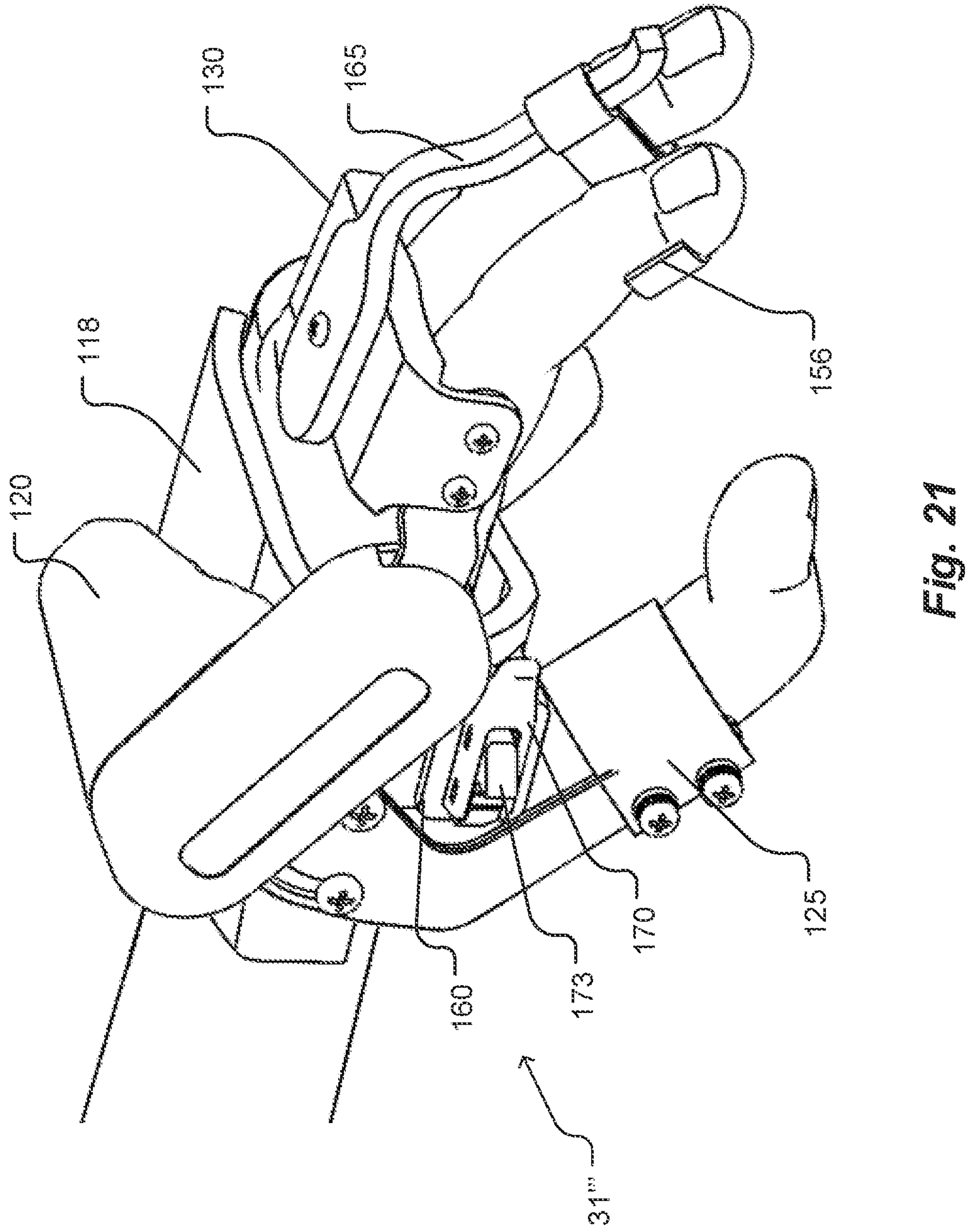
FIG. 21 is a three-quarter (showing the front and right side) perspective view of an alternative embodiment of the hand assembly 31'", as donned on the hand of the wearer, in which the hand support shell 118 includes the locking mechanism 170 and the remainder of the hand assembly 31' forms a hand unit 2101 with an affixment member 160 for mounting the hand unit 2101 to the hand support shell 118.

In further embodiments, in which the finger carrier assembly 150 is permanently affixed to the finger support platform 130, the hand assembly 31''' is configured such that the hand support shell 118 includes the locking mechanism 170, and the remainder of the hand assembly 31' forms a hand unit 2101 with an affixment member 160 for mounting the hand unit 2101 to the hand support shell 118. FIG. 21 is a three-quarter (showing the front and right side) perspective view of an alternative embodiment of the hand assembly 31', as donned on the hand of the wearer, FIG. 22 is a three-quarter (showing the front and right side) perspective view of the hand support shell 118 used in the hand assembly 31' of FIG. 21, and FIG. 23 is a three-quarter (showing the front and right side) perspective view of the hand unit 2101 used in the hand assembly 31'' 'of FIG. 21.

Figure 22:
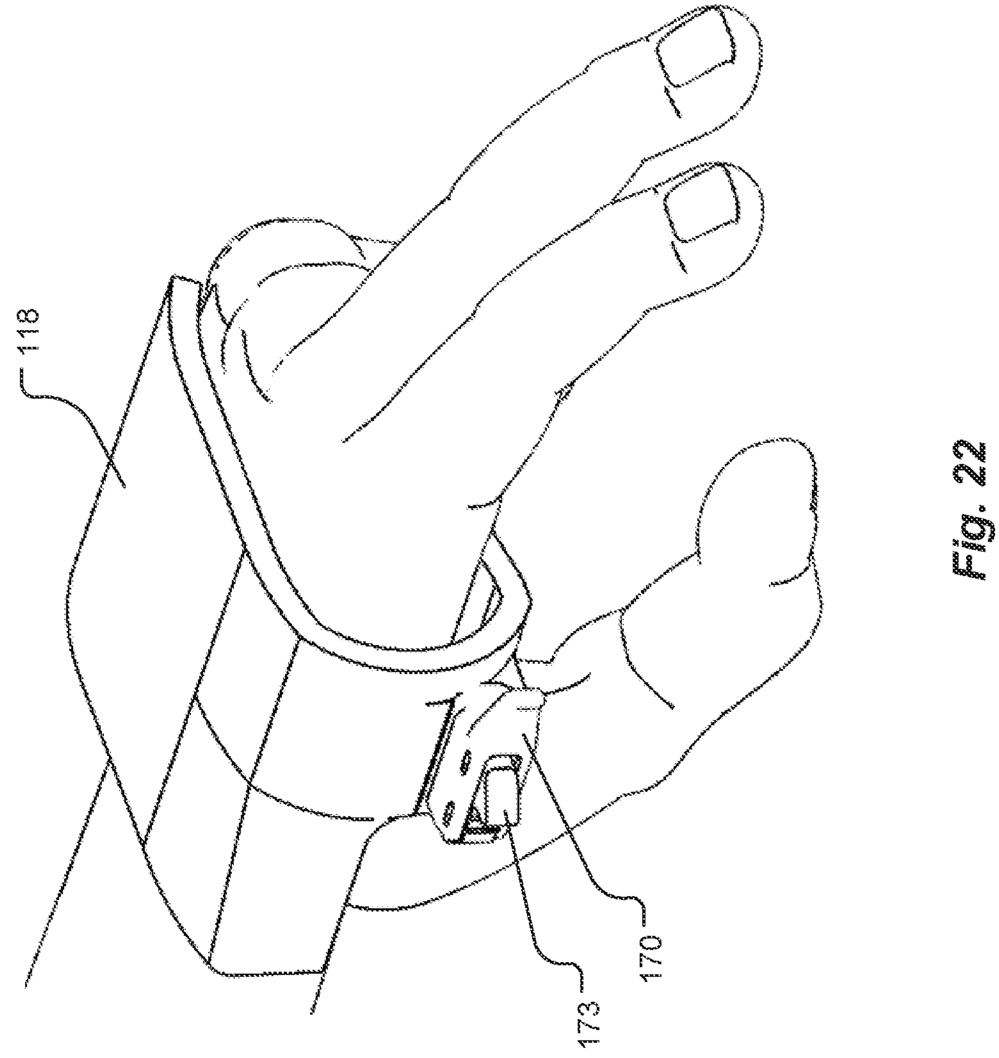
FIG. 22 is a three-quarter (showing the front and right side) perspective view of the hand support shell 118 used in the hand assembly 31'" of FIG. 21.
Figure 23:
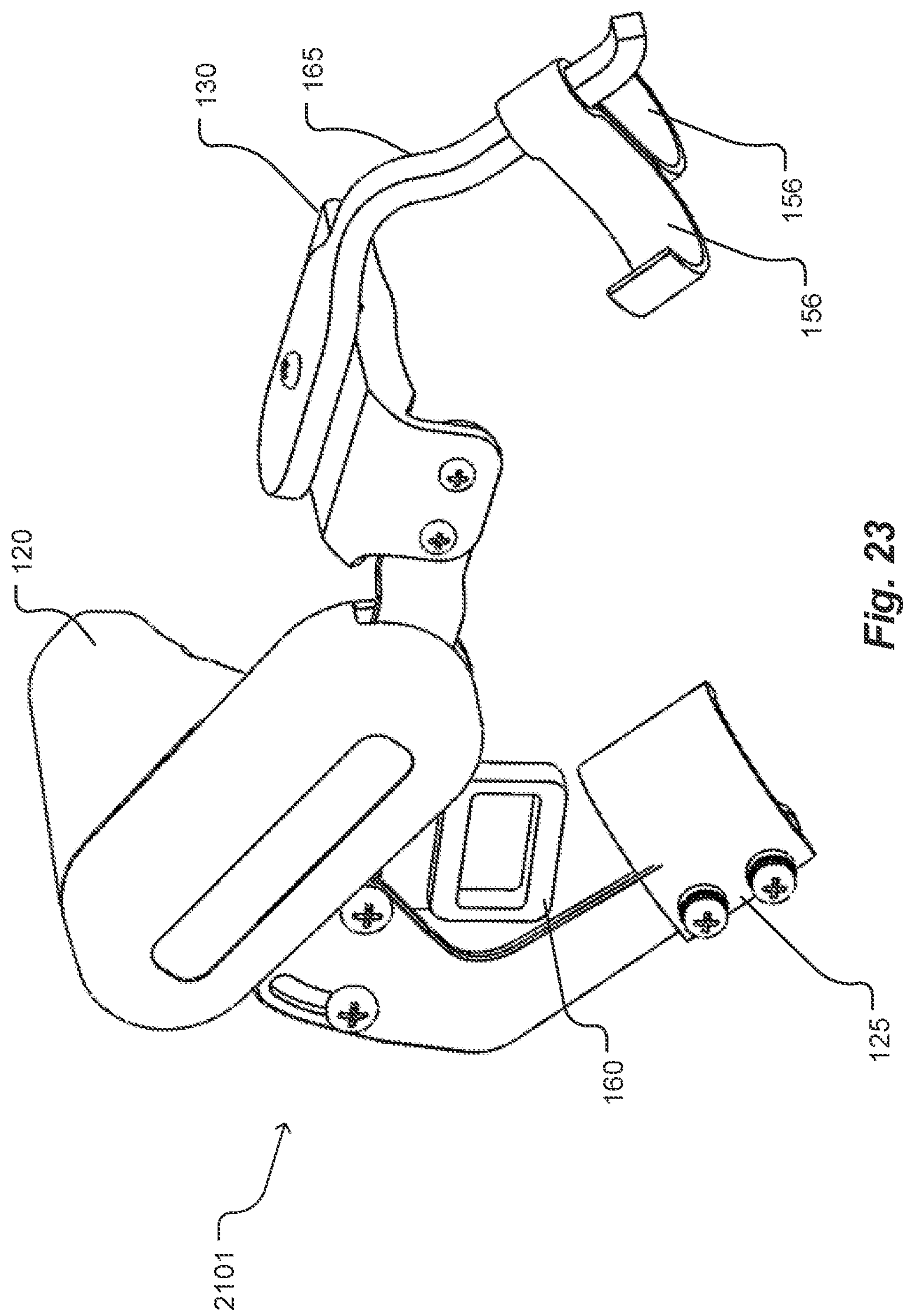
FIG. 23 is a three-quarter (showing the front and right side) perspective view of the hand unit 2101 used in the hand assembly 31'" of FIG. 21.

To don the powered orthotic device 102' of FIGS. 21-23, the wearer first guides the upper palm of the impaired hand to rest upon the interior of the hand support shell 118. Then, the wearer may position each receiver 156 of the finger carrier 155 on the hand unit 2101 under a different finger of the impaired hand. As the wearer orients the hand unit 201 to pull its affixment member 160 over the locking mechanism 170 on the hand support shell 118, the finger carrier assembly 150 straightens the curled fingers of the impaired hand. When the affixment member 160 is positioned around the base 175, the latch 172 secures the affixment member 160 and thus the hand unit 2101 to the hand support shell 118. The wearer may insert the thumb of the impaired hand into the thumb engagement member 125 coupled to the brace 110. In this manner, the wearer may use his or her free hand to affix the hand unit 2101 to the hand support shell 118, to form the hand assembly 31''', and begin operating the powered orthotic device 102.

When the wearer is finished using the powered orthotic device 102, the wearer may operate the release 173 of the locking mechanism 170 to disengage the hand unit 2101 from the hand support shell 118. The wearer slides the release 173 to retract the catch 172 into the base 175 of the locking mechanism 170. Because the catch 172 no longer retains the affixment member 160, the wearer may lift the affixment member 160 over the base 175 to detach the hand unit 2101. The wearer may further remove the impaired fingers from the finger carrier 155, and thereby allow his or her impaired hand to rest until the wearer next wishes to don the powered orthotic device 102.

Although the embodiments shown in FIGS. 21-23 depict the hand support shell 118 with the locking mechanism 170 and the hand unit 2101 with the affixment member, the positions of the locking mechanism 170 and affixment member 160 may be reversed, i.e., the locking mechanism 170 may be disposed on the hand unit 2101, while the affixment member 160 is disposed on the hand support shell 118. Moreover, the hand assembly 31''' may use any other type of affixment member 160 and/or locking mechanism 170 described herein, or equivalents as would be appreciated by one of ordinary skill in the art.

Furthermore, in the embodiments of FIGS. 21-23, the locking mechanism 170 and affixment member 160 are disposed on portions of the hand support shell 118 and hand unit 2101, respectively, to be coupled to a lateral surface of the wearer's hand. However, in other embodiments, the locking mechanism 170 and affixment member 160 may be disposed so as to be coupled to a dorsal surface of the wearer's hand.

The powered orthotic device 101 may also include actuators beyond the arm actuator 113 and hand actuator 120 depicted in FIGS. 1-13. The powered orthotic device 101 may include multiple actuators at any position where a single actuator has been depicted (e.g., multiple actuators coupled to the wearer's hand or elbow). Further actuators may be coupled to other joints of the wearer. Moreover, in some embodiments, one or more actuators may be located remotely from the joint(s) for which the actuators are aiding motion.

Various embodiments of the present invention may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

Without limitation, potential subject matter that may be claimed (prefaced with the letter "P" so as to avoid confusion with the actual claims presented below) includes:

P1. An improved powered orthotic device of the type being removably attachable to an arm of a wearer, the device including a brace, a finger engagement member, coupled to the brace, to engage a set of fingers, a thumb engagement member, and a hand actuator configured to cause motion of the finger engagement member relative to the thumb engagement member, wherein the improvement comprises:

- a finger carrier assembly affixed to the brace of the powered orthotic device, the finger carrier assembly including a finger carrier shaped to engage the set of fingers of the wearer, and
- a control, configured to be operable by a wearer of the powered orthotic device, for moving the finger carrier assembly between a first position that engages the fingers of the wearer by the finger carrier and a second position that disengages the finger carrier from the fingers of the wearer, so that the wearer can don the orthotic device, without assistance by a second person, by attaching the orthotic device to the arm of the wearer and using a free hand of the wearer to operate the control to move the finger carrier assembly to the first position to engage the fingers of the wearer.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. An improved powered orthotic device of the type being removably attachable to an arm of a wearer, the device including a brace, a finger engagement member, coupled to the brace, to engage a set of fingers, a thumb engagement member, and a hand actuator configured to cause motion of the finger engagement member relative to the thumb engagement member, wherein the improvement comprises:

the finger engagement member including:

a finger carrier shaped to engage the set of fingers of the wearer;

an affixment member coupled to a component selected from the group consisting of the brace and the finger carrier; and a locking mechanism configured (a) to be toggled between an unlocked position and a locked position and (b) to be removably attached to the affixment member;

so that the wearer can don the orthotic device, without assistance by a second person, by attaching the orthotic device to the arm of the wearer, placing the set of fingers into the finger carrier, and using a free hand of the wearer to stabilize the set of fingers in relation to the brace by causing the locking mechanism to engage with the affixment member and to thereafter toggle to the locked position.

2. The orthotic device of claim 1, wherein the affixment member includes a loop and the locking mechanism includes a catch that removably retains the loop.

3. The orthotic device of claim 2, wherein the catch is spring-loaded in a latched position.

4. The orthotic device of claim 2, wherein the locking mechanism further includes a release configured to disengage the loop from the catch.

5. The orthotic device of claim 4, wherein the release is configured to slide between a latched position that retains the loop and an unlatched position that disengages the loop.

6. The orthotic device of claim 1, wherein the affixment member includes a dual side release buckle and the locking mechanism includes a catch that is configured to removably retain the dual side release buckle.

7. The orthotic device of claim 1, wherein the locking mechanism removably attaches to the affixment member via magnetic force.

8. The orthotic device of claim 1, wherein the locking mechanism removably attaches to the affixment member via friction fit.

9. The orthotic device of claim 1, wherein the finger carrier includes a plurality of receivers configured to receive a different finger in each receiver of the plurality of receivers.

10. The orthotic device of claim 9, wherein each receiver in the plurality of receivers is a groove configured to receive a respective finger along a length of the groove and the receiver being open on at least one side such that a respective finger of the wearer can be inserted, transversely to the length of the receiver, from the at least one side of the receiver into the groove.

11. The orthotic device of claim 1, further comprising a grip, permanently attached to the finger carrier, that is configured to provide an increased surface area for contacting an object, relative to the finger carrier.

12. The orthotic device of claim 11, wherein the grip includes a rigid plate.

13. The orthotic device of claim 11, wherein an underside of the grip has a textured surface to increase friction between the grip and an object to be grasped.

14. The orthotic device of claim 1, wherein the affixment member is disposed on a portion of the brace that is configured to be coupled to (1) a dorsal surface of the wearer's hand or (2) a lateral surface of the wearer's hand.

15. The orthotic device of claim 1, further comprising a hand support shell configured to receive a hand of the wearer therethrough, wherein the locking mechanism is attached to the hand support shell, the affixment member is affixed to the brace, and the locking mechanism is configured to be removably affixed to the affixment member to stabilize the set of fingers in relation to the brace.

16. The orthotic device of claim 1, wherein the locking mechanism is affixed to the brace, and the affixment member is configured to be removably attached to the locking mechanism to stabilize the set of fingers in relation to the brace.

17. The orthotic device of claim 16, wherein the locking mechanism includes a latch.

18. The orthotic device of claim 16, wherein the latch is spring-loaded.

* * * * *